US012658315B2

(12) United States Patent
Valentine et al.

(10) Patent No.: US 12,658,315 B2
(45) Date of Patent: \*Jun. 16, 2026

(54) MANAGED MEDICAL INFORMATION EXCHANGE

(71) Applicant: BAXTER CORPORATION ENGLEWOOD, Englewood, CO (US)

(72) Inventors: Matthew A. Valentine, Ormond Beach, FL (US); Bhavesh Padmani, Port Orange, FL (US); Robert Bossio, Palm Coast, FL (US); Kristina Yevseyeva, Daytona Beach, FL (US); Srinivas Modekurti, Buffalo Grove, IL (US)

(73) Assignee: BAXTER CORPORATION ENGLEWOOD, Englewood, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/845,380

(22) Filed: Jun. 21, 2022

(65) Prior Publication Data

US 2022/0319719 A1 Oct. 6, 2022

Related U.S. Application Data

(63) Continuation of application No. 14/753,712, filed on Jun. 29, 2015, now Pat. No. 11,367,533.

(Continued)

(51) Int. Cl.
*G16H 40/67* (2018.01)
*G16H 10/60* (2018.01)
(Continued)

(52) U.S. Cl.
CPC ............. *G16H 40/67* (2018.01); *G16H 10/60* (2018.01); *H04L 9/3242* (2013.01);
(Continued)

(58) Field of Classification Search
None
See application file for complete search history.

(56) References Cited

U.S. PATENT DOCUMENTS

| | | | |
|---|---|---|---|
| 641,748 | A | 1/1900 | Smith |
| 819,339 | A | 5/1906 | Cleland |

(Continued)

FOREIGN PATENT DOCUMENTS

| | | |
|---|---|---|
| CN | 1516257 | 5/1999 |
| CN | 2440518 | 8/2001 |

(Continued)

OTHER PUBLICATIONS

Heurix, M. Karlinger and T. Neubauer, "Pseudonymization with Metadata Encryption for Privacy-Preserving Searchable Documents," 2012 45th Hawaii International Conference on System Sciences, Maui, HI, USA, 2012, pp. 3011-3020, doi: 10.1109/HICSS. 2012.491 (Year: 2012).*

(Continued)

*Primary Examiner* — Rachel L. Porter
(74) *Attorney, Agent, or Firm* — K&L Gates LLP

(57) ABSTRACT

A managed medical information exchange system is disclosed. In an example, an exchange system is configured to manage medical information by redacting a portion of medical records. The medical information may have patient identifying information and/or protected health information (PHI) removed therefrom prior to being stored in a shareable data portion for access by users. Further still, the medical information in the shareable data portion may be formatted according to an identity of a user accessing the data, a context in which the data is to be used, and/or a requested format of the data. In turn, the exchange of medical information may facilitate data analytics that may serve a variety of beneficial purposes.

20 Claims, 5 Drawing Sheets

Related U.S. Application Data

(60) Provisional application No. 62/019,227, filed on Jun. 30, 2014.

(51) Int. Cl.

| | |
| --- | --- |
| *H04L 9/32* | (2006.01) |
| *H04W 12/03* | (2021.01) |
| G06Q 10/087 | (2023.01) |
| G16H 20/10 | (2018.01) |
| G16H 70/20 | (2018.01) |
| G16H 70/40 | (2018.01) |

(52) U.S. Cl.
CPC .......... *H04W 12/03* (2021.01); *G06Q 10/087* (2013.01); *G16H 20/10* (2018.01); *G16H 70/20* (2018.01); *G16H 70/40* (2018.01)

(56) References Cited

U.S. PATENT DOCUMENTS

| | | | |
| --- | --- | --- | --- |
| 3,426,150 | A | 2/1969 | Tygart |
| 3,739,943 | A | 6/1973 | Williamsen et al. |
| 3,742,938 | A | 7/1973 | Stern |
| 3,756,752 | A | 9/1973 | Stenner |
| 3,774,762 | A | 11/1973 | Lichtenstein |
| 3,786,190 | A | 1/1974 | Pori |
| 3,809,871 | A | 5/1974 | Howard et al. |
| 3,810,102 | A | 5/1974 | Parks, III et al. |
| 3,848,112 | A | 11/1974 | Weichselbaum et al. |
| 3,858,574 | A | 1/1975 | Page |
| 3,878,967 | A | 4/1975 | Joslin et al. |
| 3,910,257 | A | 10/1975 | Fletcher et al. |
| 3,910,260 | A | 10/1975 | Sarnoff et al. |
| 3,921,196 | A | 11/1975 | Patterson |
| 3,971,000 | A | 7/1976 | Cromwell |
| 3,995,630 | A | 12/1976 | Verrdonk |
| 3,998,103 | A | 12/1976 | Bjorklund et al. |
| 4,032,908 | A | 6/1977 | Rice et al. |
| 4,078,562 | A | 3/1978 | Friedman |
| 4,144,496 | A | 3/1979 | Cunningham et al. |
| 4,151,407 | A | 4/1979 | McBride et al. |
| 4,156,867 | A | 5/1979 | Bench et al. |
| 4,164,320 | A | 8/1979 | Irazoqui et al. |
| 4,173,971 | A | 11/1979 | Karz |
| 4,199,307 | A | 4/1980 | Jassawalla |
| 4,270,532 | A | 6/1981 | Franetzki et al. |
| 4,273,121 | A | 6/1981 | Jassawalla |
| 4,282,872 | A | 8/1981 | Franetzki et al. |
| 4,308,866 | A | 1/1982 | Jelliffe et al. |
| 4,319,338 | A | 3/1982 | Grudowski et al. |
| 4,320,757 | A | 3/1982 | Whitney et al. |
| 4,354,252 | A | 10/1982 | Lamb et al. |
| 4,369,780 | A | 1/1983 | Sakai |
| 4,370,983 | A | 2/1983 | Lichtenstein |
| 4,373,527 | A | 2/1983 | Fischell |
| 4,381,776 | A | 5/1983 | Latham, Jr. |
| 4,385,630 | A | 5/1983 | Gilcher et al. |
| 4,398,289 | A | 8/1983 | Schoate |
| 4,398,908 | A | 8/1983 | Siposs |
| 4,414,566 | A | 11/1983 | Peyton et al. |
| 4,416,654 | A | 11/1983 | Schoendorfer et al. |
| 4,425,114 | A | 1/1984 | Schoendorfer et al. |
| 4,428,381 | A | 1/1984 | Hepp |
| 4,443,216 | A | 4/1984 | Chappell |
| 4,447,224 | A | 5/1984 | DeCant, Jr. et al. |
| 4,449,538 | A | 5/1984 | Corbitt et al. |
| 4,451,255 | A | 5/1984 | Bujan et al. |
| 4,457,750 | A | 7/1984 | Hill |
| 4,458,693 | A | 7/1984 | Badzinski et al. |
| 4,460,358 | A | 7/1984 | Somerville et al. |
| 4,464,172 | A | 8/1984 | Lichtenstein |
| 4,469,481 | A | 9/1984 | Kobayashi |
| 4,475,901 | A | 10/1984 | Kraegen et al. |
| 4,476,381 | A | 10/1984 | Rubin |
| 4,480,751 | A | 11/1984 | Lueptow |
| 4,481,670 | A | 11/1984 | Freeburg |
| 4,487,604 | A | 12/1984 | Iwatschenko et al. |
| 4,490,798 | A | 12/1984 | Franks et al. |
| 4,496,351 | A | 1/1985 | Hillel et al. |
| 4,511,352 | A | 4/1985 | Theeuwes et al. |
| 4,525,861 | A | 6/1985 | Freeburg |
| 4,529,401 | A | 7/1985 | Leslie et al. |
| 4,531,527 | A | 7/1985 | Reinhold, Jr. et al. |
| 4,538,138 | A | 8/1985 | Harvey et al. |
| 4,545,071 | A | 10/1985 | Freeburg |
| 4,551,133 | A | 11/1985 | Zegers de Beyl et al. |
| 4,559,038 | A | 12/1985 | Berg et al. |
| 4,560,979 | A | 12/1985 | Rosskopf |
| 4,561,443 | A | 12/1985 | Hogrefe et al. |
| 4,562,751 | A | 1/1986 | Nason |
| 4,564,054 | A | 1/1986 | Gustavsson |
| 4,590,473 | A | 5/1986 | Burke et al. |
| 4,602,249 | A | 7/1986 | Abbott |
| 4,619,653 | A | 10/1986 | Fischell |
| 4,622,979 | A | 11/1986 | Katchis et al. |
| 4,624,661 | A | 11/1986 | Arimond |
| 4,636,950 | A | 1/1987 | Caswell et al. |
| 4,637,817 | A | 1/1987 | Archibald et al. |
| 4,650,469 | A | 3/1987 | Berg et al. |
| 4,652,262 | A | 3/1987 | Veracchi |
| 4,653,010 | A | 3/1987 | Figler et al. |
| 4,676,776 | A | 6/1987 | Howson |
| 4,681,563 | A | 7/1987 | Deckert et al. |
| 4,688,167 | A | 8/1987 | Agarwal |
| 4,691,580 | A | 9/1987 | Fosslien |
| 4,695,954 | A | 9/1987 | Rose et al. |
| 4,696,671 | A | 9/1987 | Epstein et al. |
| 4,697,928 | A | 10/1987 | Csongor |
| 4,702,595 | A | 10/1987 | Mutschler et al. |
| 4,705,506 | A | 11/1987 | Archibald |
| D293,135 | S | 12/1987 | Medema et al. |
| 4,714,462 | A | 12/1987 | DiComenico |
| 4,717,042 | A | 1/1988 | McLaughlin |
| 4,718,576 | A | 1/1988 | Tamura et al. |
| 4,722,224 | A | 2/1988 | Scheller et al. |
| 4,722,349 | A | 2/1988 | Baumberg |
| 4,722,734 | A | 2/1988 | Kolln |
| 4,730,849 | A | 3/1988 | Siegel |
| 4,731,058 | A | 3/1988 | Doan |
| 4,732,411 | A | 3/1988 | Siegel |
| 4,741,732 | A | 5/1988 | Crankshaw et al. |
| 4,741,736 | A | 5/1988 | Brown |
| 4,756,706 | A | 7/1988 | Kerns et al. |
| 4,759,756 | A | 7/1988 | Forman |
| 4,778,449 | A | 10/1988 | Weber et al. |
| 4,779,626 | A | 10/1988 | Peel et al. |
| 4,784,645 | A | 11/1988 | Fischell |
| 4,785,799 | A | 11/1988 | Schoon et al. |
| 4,785,969 | A | 11/1988 | McLaughlin |
| 4,796,644 | A | 1/1989 | Polaschegg |
| 4,797,840 | A | 1/1989 | Fraden |
| 4,803,625 | A | 2/1989 | Fu et al. |
| 4,810,090 | A | 3/1989 | Boucher |
| 4,810,243 | A | 3/1989 | Howson |
| 4,811,844 | A | 3/1989 | Moulding, Jr. et al. |
| 4,816,208 | A | 3/1989 | Woods et al. |
| 4,817,044 | A | 3/1989 | Ogren |
| 4,828,545 | A | 5/1989 | Epstein et al. |
| 4,829,524 | A | 5/1989 | Yoshida |
| 4,830,018 | A | 5/1989 | Treach |
| 4,831,562 | A | 5/1989 | Mcintosh et al. |
| 4,832,033 | A | 5/1989 | Maher et al. |
| 4,835,372 | A | 5/1989 | Gombrich et al. |
| 4,835,521 | A | 5/1989 | Andrejasich et al. |
| 4,838,275 | A | 6/1989 | Lee |
| 4,839,806 | A | 6/1989 | Goldfischer et al. |
| 4,845,644 | A | 7/1989 | Anthias et al. |
| 4,847,764 | A | 7/1989 | Halvorson |
| 4,850,009 | A | 7/1989 | Zook et al. |
| 4,850,972 | A | 7/1989 | Schulman et al. |
| 4,853,521 | A | 8/1989 | Claeys et al. |
| 4,854,324 | A | 8/1989 | Hirschman et al. |
| 4,857,713 | A | 8/1989 | Brown |
| 4,857,716 | A | 8/1989 | Gombrich et al. |

(56)  References Cited

U.S. PATENT DOCUMENTS

| | | | |
|---|---|---|---|
| 4,865,584 A | 9/1989 | Epstein et al. |
| 4,871,351 A | 10/1989 | Feingold |
| 4,878,175 A | 10/1989 | Norden-Paul et al. |
| 4,889,132 A | 12/1989 | Hutcheson et al. |
| 4,889,134 A | 12/1989 | Greenwold et al. |
| 4,893,270 A | 1/1990 | Beck et al. |
| 4,897,777 A | 1/1990 | Janke et al. |
| 4,898,209 A | 2/1990 | Zbed |
| 4,898,576 A | 2/1990 | Philip |
| 4,898,578 A | 2/1990 | Rubalcaba, Jr. |
| 4,901,728 A | 2/1990 | Hutchison |
| 4,908,017 A | 3/1990 | Howson et al. |
| 4,912,623 A | 3/1990 | Rantala et al. |
| 4,916,441 A | 4/1990 | Gombrich et al. |
| 4,922,922 A | 5/1990 | Pollock et al. |
| 4,925,444 A | 5/1990 | Orkin et al. |
| 4,933,843 A | 6/1990 | Scheller et al. |
| 4,937,777 A | 6/1990 | Flood et al. |
| 4,941,808 A | 7/1990 | Qureshi et al. |
| 4,943,279 A | 7/1990 | Samiotes et al. |
| 4,946,445 A | 8/1990 | Lynn |
| 4,949,274 A | 8/1990 | Hollander et al. |
| 4,952,928 A | 8/1990 | Carroll et al. |
| 4,953,074 A | 8/1990 | Kametani et al. |
| 4,960,230 A | 10/1990 | Marelli |
| 4,966,579 A | 10/1990 | Polaschegg |
| 4,967,928 A | 11/1990 | Carter |
| 4,968,295 A | 11/1990 | Neumann |
| 4,977,590 A | 12/1990 | Milovancevic |
| 4,978,335 A | 12/1990 | Arthur, III |
| 4,991,091 A | 2/1991 | Allen |
| 4,992,926 A | 2/1991 | Janke et al. |
| 4,993,068 A | 2/1991 | Piosenka et al. |
| 4,993,506 A | 2/1991 | Angel |
| 4,998,249 A | 3/1991 | Bennett et al. |
| 5,002,055 A | 3/1991 | Merki et al. |
| 5,003,296 A | 3/1991 | Lee |
| 5,006,699 A | 4/1991 | Felkner et al. |
| 5,007,429 A | 4/1991 | Treatch et al. |
| 5,012,402 A | 4/1991 | Akiyama |
| 5,012,411 A | 4/1991 | Policastro et al. |
| 5,014,875 A | 5/1991 | Mclaughlin et al. |
| 5,016,172 A | 5/1991 | Dessertine |
| 5,023,770 A | 6/1991 | Siverling |
| 5,025,374 A | 6/1991 | Roizen et al. |
| 5,036,852 A | 8/1991 | Leishman |
| 5,038,800 A | 8/1991 | Oba |
| 5,041,086 A | 8/1991 | Koenig et al. |
| 5,045,048 A | 9/1991 | Kaleskas et al. |
| 5,047,959 A | 9/1991 | Phillips et al. |
| 5,053,031 A | 10/1991 | Borsanyi |
| 5,053,990 A | 10/1991 | Kreifels et al. |
| 5,055,001 A | 10/1991 | Natwick et al. |
| 5,057,076 A | 10/1991 | Polaschegg |
| 5,061,243 A | 10/1991 | Winchell et al. |
| 5,072,356 A | 12/1991 | Watt et al. |
| 5,072,383 A | 12/1991 | Brimm et al. |
| 5,072,412 A | 12/1991 | Henderson, Jr. et al. |
| 5,078,683 A | 1/1992 | Sancoff et al. |
| 5,084,828 A | 1/1992 | Kaufman et al. |
| 5,087,245 A | 2/1992 | Doan |
| 5,088,904 A | 2/1992 | Okada |
| 5,088,981 A | 2/1992 | Howson et al. |
| 5,088,990 A | 2/1992 | Hivale et al. |
| 5,096,385 A | 3/1992 | Georgi et al. |
| 5,098,377 A | 3/1992 | Borsanyi et al. |
| 5,100,380 A | 3/1992 | Epstein et al. |
| 5,100,394 A | 3/1992 | Dudar et al. |
| 5,104,374 A | 4/1992 | Bishko et al. |
| 5,108,363 A | 4/1992 | Tuttle et al. |
| 5,108,367 A | 4/1992 | Epstein et al. |
| 5,108,372 A | 4/1992 | Swenson |
| 5,109,487 A | 4/1992 | Ohgomori et al. |
| 5,109,849 A | 5/1992 | Goodman et al. |
| 5,112,319 A | 5/1992 | Lai |
| 5,116,203 A | 5/1992 | Natwick et al. |
| 5,116,312 A | 5/1992 | Blankenship et al. |
| 5,131,092 A | 7/1992 | Sackmann et al. |
| 5,134,574 A | 7/1992 | Beaverstock et al. |
| 5,135,500 A | 8/1992 | Zdeb |
| 5,137,023 A | 8/1992 | Mendelson et al. |
| 5,151,978 A | 9/1992 | Bronikowski et al. |
| 5,152,296 A | 10/1992 | Simons |
| 5,153,416 A | 10/1992 | Neeley |
| 5,153,827 A | 10/1992 | Coutre et al. |
| 5,155,693 A | 10/1992 | Altmayer et al. |
| 5,157,595 A | 10/1992 | Lovrenich |
| 5,158,091 A | 10/1992 | Butterfield et al. |
| 5,159,673 A | 10/1992 | Sackmann et al. |
| 5,160,320 A | 11/1992 | Yum et al. |
| 5,161,211 A | 11/1992 | Taguchi et al. |
| 5,167,235 A | 12/1992 | Seacord et al. |
| 5,169,642 A | 12/1992 | Brinker et al. |
| 5,172,698 A | 12/1992 | Stanko |
| 5,176,004 A | 1/1993 | Gaudet |
| 5,179,569 A | 1/1993 | Sawyer |
| 5,179,700 A | 1/1993 | Aihara et al. |
| 5,181,910 A | 1/1993 | Scanlon |
| 5,190,185 A | 3/1993 | Blechl |
| 5,190,522 A | 3/1993 | Wojcicki et al. |
| 5,191,891 A | 3/1993 | Righter |
| 5,208,762 A | 5/1993 | Charhut et al. |
| 5,208,907 A | 5/1993 | Shelton et al. |
| 5,211,849 A | 5/1993 | Kitaevich et al. |
| 5,213,099 A | 5/1993 | Tripp, Jr. |
| 5,213,232 A | 5/1993 | Kraft et al. |
| 5,213,568 A | 5/1993 | Lattin et al. |
| 5,219,330 A | 6/1993 | Bollish et al. |
| 5,219,331 A | 6/1993 | Vanderveen |
| 5,225,974 A | 7/1993 | Mathews et al. |
| 5,226,425 A | 7/1993 | Righter |
| 5,228,450 A | 7/1993 | Sellers |
| 5,231,990 A | 8/1993 | Gauglitz |
| 5,234,404 A | 8/1993 | Tuttle et al. |
| 5,235,510 A | 8/1993 | Yamada et al. |
| 5,236,416 A | 8/1993 | McDaniel et al. |
| 5,238,001 A | 8/1993 | Gallant et al. |
| 5,240,007 A | 8/1993 | Pytel et al. |
| 5,244,463 A | 9/1993 | Cordner, Jr. et al. |
| 5,245,704 A | 9/1993 | Weber et al. |
| 5,254,096 A | 10/1993 | Rondelet et al. |
| 5,256,156 A | 10/1993 | Kern et al. |
| 5,256,157 A | 10/1993 | Samiotes et al. |
| 5,265,010 A | 11/1993 | Evans-Paganelli et al. |
| 5,265,431 A | 11/1993 | Gaudet et al. |
| 5,267,174 A | 11/1993 | Kaufman et al. |
| 5,271,405 A | 12/1993 | Boyer et al. |
| 5,272,318 A | 12/1993 | Gorman |
| 5,272,321 A | 12/1993 | Otsuka et al. |
| 5,273,517 A | 12/1993 | Barone et al. |
| 5,277,188 A | 1/1994 | Selker |
| 5,283,861 A | 2/1994 | Dangler et al. |
| 5,284,150 A | 2/1994 | Butterfield et al. |
| 5,286,252 A | 2/1994 | Tuttle et al. |
| 5,292,029 A | 3/1994 | Pearson |
| 5,297,257 A | 3/1994 | Struger et al. |
| 5,298,021 A | 3/1994 | Sherer |
| 5,304,126 A | 4/1994 | Epstein et al. |
| 5,307,263 A | 4/1994 | Brown |
| 5,307,372 A | 4/1994 | Sawyer et al. |
| 5,307,463 A | 4/1994 | Hyatt et al. |
| 5,311,908 A | 5/1994 | Barone et al. |
| 5,314,243 A | 5/1994 | McDonald et al. |
| 5,315,505 A | 5/1994 | Pratt et al. |
| 5,317,506 A | 5/1994 | Coutre et al. |
| 5,319,363 A | 6/1994 | Welch et al. |
| 5,319,543 A | 6/1994 | Wilhelm |
| 5,321,618 A | 6/1994 | Gessman |
| 5,321,829 A | 6/1994 | Zifferer |
| 5,324,422 A | 6/1994 | Colleran et al. |
| 5,325,478 A | 6/1994 | Shelton et al. |
| 5,327,341 A | 7/1994 | Whalen et al. |
| 5,331,549 A | 7/1994 | Crawford, Jr. |
| 5,336,245 A | 8/1994 | Adams et al. |

(56) References Cited

U.S. PATENT DOCUMENTS

| | | | |
|---|---|---|---|
| 5,337,230 A | 8/1994 | Baumgartner et al. |
| 5,337,919 A | 8/1994 | Spaulding et al. |
| 5,338,157 A | 8/1994 | Blomquist |
| 5,339,421 A | 8/1994 | Housel, III |
| 5,339,821 A | 8/1994 | Fujimoto |
| 5,341,291 A | 8/1994 | Roizen et al. |
| 5,341,412 A | 8/1994 | Ramot et al. |
| 5,348,008 A | 9/1994 | Bornn et al. |
| 5,348,539 A | 9/1994 | Herskowitz |
| 5,349,675 A | 9/1994 | Fitzgerald et al. |
| 5,356,378 A | 10/1994 | Doan |
| 5,361,202 A | 11/1994 | Doue |
| 5,361,758 A | 11/1994 | Hall et al. |
| 5,366,896 A | 11/1994 | Margrey et al. |
| 5,366,904 A | 11/1994 | Qureshi et al. |
| 5,367,555 A | 11/1994 | Isoyama |
| 5,368,562 A | 11/1994 | Blomquist et al. |
| 5,370,612 A | 12/1994 | Maeda et al. |
| 5,371,687 A | 12/1994 | Holmes, II et al. |
| 5,374,251 A | 12/1994 | Smith |
| 5,374,813 A | 12/1994 | Shipp |
| 5,374,965 A | 12/1994 | Kanno |
| 5,375,604 A | 12/1994 | Kelly et al. |
| 5,376,070 A | 12/1994 | Purvis et al. |
| 5,377,864 A | 1/1995 | Blechl et al. |
| 5,378,231 A | 1/1995 | Johnson et al. |
| 5,379,214 A | 1/1995 | Arbuckle et al. |
| 5,389,078 A | 2/1995 | Zalesky et al. |
| 5,390,238 A | 2/1995 | Kirk et al. |
| 5,392,951 A | 2/1995 | Gardner et al. |
| 5,395,320 A | 3/1995 | Padda et al. |
| 5,395,321 A | 3/1995 | Kawahara et al. |
| 5,398,336 A | 3/1995 | Tantry et al. |
| 5,401,059 A | 3/1995 | Ferrario |
| 5,404,292 A | 4/1995 | Hendrickson |
| 5,404,384 A | 4/1995 | Colburn et al. |
| 5,406,473 A | 4/1995 | Yoshikura et al. |
| 5,412,715 A | 5/1995 | Volpe |
| 5,415,167 A | 5/1995 | Wilk |
| 5,416,695 A | 5/1995 | Stutman et al. |
| 5,417,222 A | 5/1995 | Dempsey et al. |
| 5,420,977 A | 5/1995 | Sztipanovits et al. |
| 5,421,343 A | 6/1995 | Feng |
| 5,423,746 A | 6/1995 | Burkett et al. |
| 5,429,602 A | 7/1995 | Hauser |
| 5,431,201 A | 7/1995 | Torchia et al. |
| 5,431,299 A | 7/1995 | Brewer et al. |
| 5,431,627 A | 7/1995 | Pastrone et al. |
| 5,433,736 A | 7/1995 | Nilsson |
| 5,438,607 A | 8/1995 | Przygoda, Jr. et al. |
| 5,440,699 A | 8/1995 | Farrand et al. |
| 5,441,047 A | 8/1995 | David et al. |
| 5,445,294 A | 8/1995 | Gardner et al. |
| 5,445,621 A | 8/1995 | Poli et al. |
| 5,446,868 A | 8/1995 | Gardea et al. |
| 5,453,098 A | 9/1995 | Botts et al. |
| 5,455,851 A | 10/1995 | Chaco et al. |
| 5,458,123 A | 10/1995 | Unger |
| 5,460,294 A | 10/1995 | Williams |
| 5,460,605 A | 10/1995 | Tuttle et al. |
| 5,461,665 A | 10/1995 | Shur et al. |
| 5,462,051 A | 10/1995 | Oka et al. |
| 5,464,392 A | 11/1995 | Epstein et al. |
| 5,465,286 A | 11/1995 | Clare et al. |
| 5,467,773 A | 11/1995 | Bergelson et al. |
| 5,468,110 A | 11/1995 | McDonald et al. |
| 5,469,855 A | 11/1995 | Pompei et al. |
| 5,471,382 A | 11/1995 | Tallman et al. |
| 5,474,552 A | 12/1995 | Palti |
| 5,482,043 A | 1/1996 | Zulauf |
| 5,482,446 A | 1/1996 | Williamson et al. |
| 5,485,408 A | 1/1996 | Blomquist |
| 5,490,610 A | 2/1996 | Pearson |
| 5,494,592 A | 2/1996 | Latham, Jr. et al. |
| 5,496,265 A | 3/1996 | Langley et al. |
| 5,496,273 A | 3/1996 | Pastrone et al. |
| 5,502,944 A | 4/1996 | Kraft et al. |
| 5,507,412 A | 4/1996 | Ebert et al. |
| 5,508,912 A | 4/1996 | Schneiderman |
| 5,509,318 A | 4/1996 | Gomes |
| 5,509,422 A | 4/1996 | Fukami |
| 5,513,957 A | 5/1996 | O'Leary |
| 5,514,088 A | 5/1996 | Zakko |
| 5,514,095 A | 5/1996 | Brightbill et al. |
| 5,515,426 A | 5/1996 | Yacenda et al. |
| 5,520,450 A | 5/1996 | Colson, Jr. et al. |
| 5,520,637 A | 5/1996 | Pager et al. |
| 5,522,396 A | 6/1996 | Langer et al. |
| 5,522,798 A | 6/1996 | Johnson et al. |
| 5,526,428 A | 6/1996 | Arnold |
| 5,528,503 A | 6/1996 | Moore et al. |
| 5,529,063 A | 6/1996 | Hill |
| 5,531,680 A | 7/1996 | Dumas et al. |
| 5,531,697 A | 7/1996 | Olsen et al. |
| 5,531,698 A | 7/1996 | Olsen |
| 5,533,079 A | 7/1996 | Colburn et al. |
| 5,533,981 A | 7/1996 | Mandro et al. |
| 5,534,691 A | 7/1996 | Holdaway et al. |
| 5,536,084 A | 7/1996 | Curtis et al. |
| 5,537,313 A | 7/1996 | Pirelli |
| 5,537,853 A | 7/1996 | Finburgh et al. |
| 5,542,420 A | 8/1996 | Goldman et al. |
| 5,544,649 A | 8/1996 | David et al. |
| 5,544,651 A | 8/1996 | Wilk |
| 5,544,661 A | 8/1996 | Davis et al. |
| 5,545,140 A | 8/1996 | Conero et al. |
| 5,546,580 A | 8/1996 | Seliger et al. |
| 5,547,470 A | 8/1996 | Johnson et al. |
| 5,549,117 A | 8/1996 | Tacklind et al. |
| 5,549,460 A | 8/1996 | O'Leary |
| 5,553,609 A | 9/1996 | Chen et al. |
| 5,558,638 A | 9/1996 | Evers et al. |
| 5,558,640 A | 9/1996 | Pfeiler et al. |
| 5,560,352 A | 10/1996 | Heim et al. |
| 5,562,232 A | 10/1996 | Pearson |
| 5,562,621 A | 10/1996 | Claude et al. |
| 5,563,347 A | 10/1996 | Martin et al. |
| 5,564,803 A | 10/1996 | McDonald et al. |
| 5,568,912 A | 10/1996 | Minami et al. |
| 5,569,186 A | 10/1996 | Lord et al. |
| 5,569,187 A | 10/1996 | Kaiser |
| 5,571,258 A | 11/1996 | Pearson |
| 5,573,502 A | 11/1996 | LeCocq et al. |
| 5,573,506 A | 11/1996 | Vasko |
| 5,575,632 A | 11/1996 | Morris et al. |
| 5,576,952 A | 11/1996 | Stutman et al. |
| 5,579,001 A | 11/1996 | Dempsey et al. |
| 5,579,378 A | 11/1996 | Arlinghaus, Jr. |
| 5,581,369 A | 12/1996 | Righter et al. |
| 5,581,687 A | 12/1996 | Lyle et al. |
| 5,582,593 A | 12/1996 | Hultman |
| 5,583,758 A | 12/1996 | Mcilroy et al. |
| 5,588,815 A | 12/1996 | Zaleski, II |
| 5,589,932 A | 12/1996 | Garcia-Rubio et al. |
| 5,590,648 A | 1/1997 | Mitchell et al. |
| 5,593,267 A | 1/1997 | McDonald et al. |
| 5,594,637 A | 1/1997 | Eisenberg et al. |
| 5,594,786 A | 1/1997 | Chaco et al. |
| 5,597,995 A | 1/1997 | Williams et al. |
| 5,598,536 A | 1/1997 | Slaughter, III et al. |
| 5,601,445 A | 2/1997 | Schipper et al. |
| 5,609,575 A | 3/1997 | Larson et al. |
| 5,609,576 A | 3/1997 | Voss et al. |
| 5,613,115 A | 3/1997 | Gihl et al. |
| 5,619,428 A | 4/1997 | Lee et al. |
| 5,619,991 A | 4/1997 | Sloane |
| 5,623,652 A | 4/1997 | Vora et al. |
| 5,623,925 A | 4/1997 | Swenson et al. |
| 5,626,144 A | 5/1997 | Tacklind et al. |
| 5,628,619 A | 5/1997 | Wilson |
| 5,630,710 A | 5/1997 | Tune et al. |
| 5,631,844 A | 5/1997 | Margrey et al. |
| 5,633,910 A | 5/1997 | Cohen |
| D380,260 S | 6/1997 | Hyman |

(56) References Cited

U.S. PATENT DOCUMENTS

| | | | |
|---|---|---|---|
| 5,634,893 A | 6/1997 | Rishton |
| 5,637,082 A | 6/1997 | Pages et al. |
| 5,637,093 A | 6/1997 | Hyman et al. |
| 5,640,301 A | 6/1997 | Roecher et al. |
| 5,640,953 A | 6/1997 | Bishop et al. |
| 5,641,628 A | 6/1997 | Bianchi |
| 5,643,193 A | 7/1997 | Papillon et al. |
| 5,643,212 A | 7/1997 | Coutre et al. |
| 5,647,853 A | 7/1997 | Feldmann et al. |
| 5,647,854 A | 7/1997 | Olsen et al. |
| 5,651,775 A | 7/1997 | Walker et al. |
| 5,652,566 A | 7/1997 | Lambert |
| 5,658,240 A | 8/1997 | Urdahl et al. |
| 5,658,250 A | 8/1997 | Blomquist et al. |
| 5,661,978 A | 9/1997 | Holmes et al. |
| 5,664,270 A | 9/1997 | Bell et al. |
| 5,666,404 A | 9/1997 | Ciccotelli et al. |
| D385,646 S | 10/1997 | Chan |
| 5,678,562 A | 10/1997 | Sellers |
| 5,678,568 A | 10/1997 | Uchikubo et al. |
| 5,681,285 A | 10/1997 | Ford et al. |
| 5,682,526 A | 10/1997 | Smokoff et al. |
| 5,683,367 A | 11/1997 | Jordan et al. |
| 5,685,844 A | 11/1997 | Marttila |
| 5,687,717 A | 11/1997 | Halpern |
| 5,687,734 A | 11/1997 | Dempsey et al. |
| 5,695,473 A | 12/1997 | Olsen |
| 5,697,951 A | 12/1997 | Harpstead |
| 5,700,998 A | 12/1997 | Palti |
| 5,701,894 A | 12/1997 | Cherry et al. |
| 5,704,351 A | 1/1998 | Mortara et al. |
| 5,704,364 A | 1/1998 | Saltzstein et al. |
| 5,704,366 A | 1/1998 | Tacklind et al. |
| 5,712,798 A | 1/1998 | Langley et al. |
| 5,712,912 A | 1/1998 | Tomko et al. |
| 5,713,485 A | 2/1998 | Liff et al. |
| 5,713,856 A | 2/1998 | Eggers et al. |
| 5,715,823 A | 2/1998 | Wood et al. |
| 5,716,114 A | 2/1998 | Holmes et al. |
| 5,716,194 A | 2/1998 | Butterfield et al. |
| 5,718,562 A | 2/1998 | Lawless et al. |
| 5,719,761 A | 2/1998 | Gatti et al. |
| RE35,743 E | 3/1998 | Pearson |
| 5,724,025 A | 3/1998 | Tavori |
| 5,724,580 A | 3/1998 | Levin et al. |
| 5,732,709 A | 3/1998 | Tacklind et al. |
| 5,733,259 A | 3/1998 | Valcke et al. |
| 5,735,887 A | 4/1998 | Barreras, Sr. et al. |
| 5,737,539 A | 4/1998 | Edelson et al. |
| 5,740,185 A | 4/1998 | Bosse |
| 5,740,800 A | 4/1998 | Hendrickson et al. |
| 5,745,366 A | 4/1998 | Higham et al. |
| 5,745,378 A | 4/1998 | Barker et al. |
| 5,752,917 A | 5/1998 | Fuchs |
| 5,752,976 A | 5/1998 | Duffin et al. |
| 5,755,563 A | 5/1998 | Clegg et al. |
| 5,758,095 A | 5/1998 | Albaum et al. |
| 5,764,923 A | 6/1998 | Tallman et al. |
| 5,766,155 A | 6/1998 | Hyman et al. |
| 5,769,811 A | 6/1998 | Stacey et al. |
| 5,771,657 A | 6/1998 | Lasher et al. |
| 5,772,585 A | 6/1998 | Lavin et al. |
| 5,772,586 A | 6/1998 | Heinonen et al. |
| 5,772,635 A | 6/1998 | Dastur et al. |
| 5,772,637 A | 6/1998 | Heinzmann et al. |
| 5,776,057 A | 7/1998 | Swenson et al. |
| 5,778,345 A | 7/1998 | McCartney |
| 5,778,882 A | 7/1998 | Raymond et al. |
| 5,781,442 A | 7/1998 | Engleson et al. |
| 5,782,805 A | 7/1998 | Meinzer et al. |
| 5,782,878 A | 7/1998 | Morgan et al. |
| 5,785,650 A | 7/1998 | Akasaka et al. |
| 5,788,669 A | 8/1998 | Peterson |
| 5,790,409 A | 8/1998 | Fedor et al. |
| 5,791,342 A | 8/1998 | Woodard |
| 5,791,880 A | 8/1998 | Wilson |
| 5,793,861 A | 8/1998 | Haigh |
| 5,793,969 A | 8/1998 | Kamentsky et al. |
| 5,795,317 A | 8/1998 | Brierton et al. |
| 5,795,327 A | 8/1998 | Wilson et al. |
| 5,797,515 A | 8/1998 | Liff et al. |
| 5,800,387 A | 9/1998 | Duffy et al. |
| 5,801,755 A | 9/1998 | Echerer |
| 5,803,906 A | 9/1998 | Pratt et al. |
| 5,805,442 A | 9/1998 | Crater et al. |
| 5,805,454 A | 9/1998 | Valerino et al. |
| 5,805,456 A | 9/1998 | Higham et al. |
| 5,805,505 A | 9/1998 | Zheng et al. |
| 5,807,321 A | 9/1998 | Stoker et al. |
| 5,807,322 A | 9/1998 | Lindsey et al. |
| 5,807,336 A | 9/1998 | Russo et al. |
| 5,810,747 A | 9/1998 | Brudny et al. |
| 5,812,410 A | 9/1998 | Lion et al. |
| 5,814,015 A | 9/1998 | Gargano et al. |
| 5,815,566 A | 9/1998 | Ramot et al. |
| 5,818,528 A | 10/1998 | Roth et al. |
| 5,822,418 A | 10/1998 | Yacenda et al. |
| 5,822,544 A | 10/1998 | Chaco et al. |
| 5,823,949 A | 10/1998 | Goltra |
| 5,826,237 A | 10/1998 | Macrae et al. |
| 5,829,438 A | 11/1998 | Gibbs et al. |
| 5,832,447 A | 11/1998 | Rieker et al. |
| 5,832,448 A | 11/1998 | Brown |
| 5,832,450 A | 11/1998 | Myers et al. |
| 5,833,599 A | 11/1998 | Schrier et al. |
| 5,841,975 A | 11/1998 | Layne et al. |
| 5,842,841 A | 12/1998 | Danby et al. |
| 5,842,976 A | 12/1998 | Williamson |
| 5,845,253 A | 12/1998 | Rensimer et al. |
| 5,848,593 A | 12/1998 | McGrady et al. |
| 5,851,186 A | 12/1998 | Wood et al. |
| 5,852,590 A | 12/1998 | De La Huerga |
| 5,853,387 A | 12/1998 | Clegg et al. |
| 5,855,550 A | 1/1999 | Lai et al. |
| 5,857,967 A | 1/1999 | Frid et al. |
| 5,859,972 A | 1/1999 | Subramaniam et al. |
| 5,865,745 A | 2/1999 | Schmitt et al. |
| 5,865,786 A | 2/1999 | Sibalis et al. |
| 5,867,821 A | 2/1999 | Ballantyne et al. |
| 5,871,465 A | 2/1999 | Vasko |
| 5,876,926 A | 3/1999 | Beecham |
| 5,880,443 A | 3/1999 | McDonald et al. |
| 5,882,338 A | 3/1999 | Gray |
| 5,883,370 A | 3/1999 | Walker et al. |
| 5,883,576 A | 3/1999 | De La Huerga |
| 5,884,273 A | 3/1999 | Sattizahn et al. |
| 5,884,457 A | 3/1999 | Ortiz et al. |
| 5,885,245 A | 3/1999 | Lynch et al. |
| 5,891,035 A | 4/1999 | Wood et al. |
| 5,891,734 A | 4/1999 | Gill et al. |
| 5,893,697 A | 4/1999 | Zimi et al. |
| 5,894,273 A | 4/1999 | Meador et al. |
| 5,895,371 A | 4/1999 | Levitas et al. |
| 5,897,493 A | 4/1999 | Brown |
| 5,897,530 A | 4/1999 | Jackson |
| 5,897,989 A | 4/1999 | Beecham |
| 5,899,665 A | 5/1999 | Makino et al. |
| 5,899,855 A | 5/1999 | Brown |
| 5,901,150 A | 5/1999 | Jhuboo et al. |
| 5,904,668 A | 5/1999 | Hyman et al. |
| 5,905,653 A | 5/1999 | Higham et al. |
| 5,907,291 A | 5/1999 | Chen et al. |
| 5,907,493 A | 5/1999 | Boyer et al. |
| 5,908,027 A | 6/1999 | Butterfield et al. |
| 5,910,107 A | 6/1999 | Iliff |
| 5,910,252 A | 6/1999 | Truitt et al. |
| 5,911,132 A | 6/1999 | Sloane |
| 5,911,687 A | 6/1999 | Sato et al. |
| 5,912,818 A | 6/1999 | McGrady et al. |
| 5,913,197 A | 6/1999 | Kameda |
| 5,913,310 A | 6/1999 | Brown |
| 5,915,089 A | 6/1999 | Stevens et al. |
| 5,915,240 A | 6/1999 | Karpf |
| 5,919,154 A | 7/1999 | Toavs et al. |

(56) References Cited

U.S. PATENT DOCUMENTS

| | | | |
|---|---|---|---|
| 5,921,938 A | 7/1999 | Aoyama et al. |
| 5,923,018 A | 7/1999 | Kameda et al. |
| 5,924,074 A | 7/1999 | Evans |
| 5,924,103 A | 7/1999 | Ahmed et al. |
| 5,927,540 A | 7/1999 | Godlewski |
| 5,931,791 A | 8/1999 | Saltzstein et al. |
| 5,935,060 A | 8/1999 | Iliff |
| 5,935,099 A | 8/1999 | Peterson et al. |
| 5,935,106 A | 8/1999 | Olsen |
| 5,938,413 A | 8/1999 | Makino et al. |
| 5,939,326 A | 8/1999 | Chupp et al. |
| 5,939,699 A | 8/1999 | Perttunen et al. |
| 5,940,306 A | 8/1999 | Gardner et al. |
| 5,940,802 A | 8/1999 | Hildebrand et al. |
| 5,941,829 A | 8/1999 | Saltzstein et al. |
| 5,942,986 A | 8/1999 | Shabot et al. |
| 5,943,423 A | 8/1999 | Muftic |
| 5,943,633 A | 8/1999 | Wilson et al. |
| 5,944,659 A | 8/1999 | Flach et al. |
| 5,945,651 A | 8/1999 | Chorosinski et al. |
| 5,946,083 A | 8/1999 | Melendez et al. |
| 5,946,659 A | 8/1999 | Lancelot et al. |
| D414,578 S | 9/1999 | Chen et al. |
| 5,950,006 A | 9/1999 | Crater et al. |
| 5,951,300 A | 9/1999 | Brown |
| 5,951,510 A | 9/1999 | Barak |
| 5,954,640 A | 9/1999 | Szabo |
| 5,954,885 A | 9/1999 | Bollish et al. |
| 5,954,971 A | 9/1999 | Pages et al. |
| 5,956,023 A | 9/1999 | Lyle et al. |
| 5,957,885 A | 9/1999 | Bollish et al. |
| 5,959,529 A | 9/1999 | Kail, IV |
| 5,960,085 A | 9/1999 | de la Huerga |
| 5,960,403 A | 9/1999 | Brown |
| 5,960,991 A | 10/1999 | Ophardt |
| 5,961,446 A | 10/1999 | Beller et al. |
| 5,961,448 A | 10/1999 | Swenson et al. |
| 5,961,487 A | 10/1999 | Davis |
| 5,963,641 A | 10/1999 | Crandall et al. |
| 5,964,700 A | 10/1999 | Tallman et al. |
| 5,966,304 A | 10/1999 | Cook et al. |
| 5,967,975 A | 10/1999 | Ridgeway |
| 5,970,423 A | 10/1999 | Langley et al. |
| 5,971,593 A | 10/1999 | McGrady |
| 5,971,921 A | 10/1999 | Timbel |
| 5,971,948 A | 10/1999 | Pages et al. |
| 5,974,124 A | 10/1999 | Schlueter, Jr. et al. |
| 5,975,737 A | 11/1999 | Crater et al. |
| 5,980,490 A | 11/1999 | Tsoukalis |
| 5,983,193 A | 11/1999 | Heinonen et al. |
| 5,987,519 A | 11/1999 | Peifer et al. |
| 5,991,731 A | 11/1999 | Colon et al. |
| 5,993,046 A | 11/1999 | McGrady et al. |
| 5,993,420 A | 11/1999 | Hyman et al. |
| 5,995,077 A | 11/1999 | Wilcox et al. |
| 5,995,965 A | 11/1999 | Experton |
| 5,997,167 A | 12/1999 | Crater et al. |
| 5,997,476 A | 12/1999 | Brown |
| 6,003,006 A | 12/1999 | Colella et al. |
| 6,004,020 A | 12/1999 | Bartur |
| 6,004,276 A | 12/1999 | Wright et al. |
| 6,006,191 A | 12/1999 | DeRienzo |
| 6,006,946 A | 12/1999 | Williams et al. |
| 6,009,333 A | 12/1999 | Chaco |
| 6,010,454 A | 1/2000 | Arieff et al. |
| 6,011,858 A | 1/2000 | Stock et al. |
| 6,011,999 A | 1/2000 | Holmes |
| 6,012,034 A | 1/2000 | Hamparian et al. |
| 6,013,057 A | 1/2000 | Danby et al. |
| 6,014,631 A | 1/2000 | Teagarden et al. |
| 6,016,444 A | 1/2000 | John |
| 6,017,318 A | 1/2000 | Gauthier et al. |
| 6,018,713 A | 1/2000 | Coli et al. |
| 6,019,745 A | 2/2000 | Gray |
| 6,021,392 A | 2/2000 | Lester et al. |
| 6,022,315 A | 2/2000 | Iliff |
| 6,023,522 A | 2/2000 | Draganoff et al. |
| 6,024,539 A | 2/2000 | Blomquist |
| 6,024,699 A | 2/2000 | Surwit et al. |
| 6,027,217 A | 2/2000 | McClure et al. |
| 6,029,138 A | 2/2000 | Khorasani et al. |
| 6,032,119 A | 2/2000 | Brown et al. |
| 6,032,155 A | 2/2000 | de la Huerga |
| 6,033,076 A | 3/2000 | Braeuning et al. |
| 6,039,251 A | 3/2000 | Holowko et al. |
| 6,039,467 A | 3/2000 | Holmes |
| 6,047,259 A | 4/2000 | Campbell et al. |
| 6,048,086 A | 4/2000 | Valerino |
| 6,050,940 A | 4/2000 | Braun et al. |
| 6,055,487 A | 4/2000 | Margery et al. |
| 6,057,758 A | 5/2000 | Dempsey et al. |
| 6,059,736 A | 5/2000 | Tapper |
| 6,061,603 A | 5/2000 | Papadopoulos et al. |
| 6,065,819 A | 5/2000 | Holmes et al. |
| 6,068,153 A | 5/2000 | Young et al. |
| 6,068,156 A | 5/2000 | Liff et al. |
| 6,073,046 A | 6/2000 | Patel et al. |
| 6,074,345 A | 6/2000 | van Oostrom et al. |
| 6,079,621 A | 6/2000 | Vardanyan et al. |
| 6,080,106 A | 6/2000 | Lloyd et al. |
| 6,081,048 A | 6/2000 | Bergmann et al. |
| 6,082,776 A | 7/2000 | Feinberg |
| 6,083,206 A | 7/2000 | Molko |
| 6,093,146 A | 7/2000 | Filangeri |
| 6,095,985 A | 8/2000 | Raymond et al. |
| 6,096,561 A | 8/2000 | Tayi |
| 6,098,892 A | 8/2000 | Peoples, Jr. |
| 6,101,407 A | 8/2000 | Groezinger |
| 6,101,478 A | 8/2000 | Brown |
| 6,102,856 A | 8/2000 | Groff et al. |
| 6,108,399 A | 8/2000 | Hernandez-Guerra et al. |
| 6,108,588 A | 8/2000 | McGrady |
| 6,109,774 A | 8/2000 | Holmes et al. |
| 6,112,224 A | 8/2000 | Peifer et al. |
| RE36,871 E | 9/2000 | Epstein et al. |
| 6,113,554 A | 9/2000 | Gilcher et al. |
| 6,116,461 A | 9/2000 | Broadfield et al. |
| 6,117,940 A | 9/2000 | Mjalli |
| 6,123,524 A | 9/2000 | Danby et al. |
| 6,125,350 A | 9/2000 | Dirbas |
| 6,129,517 A | 10/2000 | Danby et al. |
| 6,132,371 A | 10/2000 | Dempsey et al. |
| 6,134,504 A | 10/2000 | Douglas et al. |
| 6,135,949 A | 10/2000 | Russo et al. |
| 6,139,495 A | 10/2000 | De La Huerga |
| 6,141,412 A | 10/2000 | Smith et al. |
| 6,144,922 A | 11/2000 | Douglas et al. |
| 6,145,695 A | 11/2000 | Garrigues |
| 6,146,523 A | 11/2000 | Kenley et al. |
| 6,148,297 A | 11/2000 | Swor et al. |
| 6,149,063 A | 11/2000 | Reynolds et al. |
| 6,151,536 A | 11/2000 | Arnold et al. |
| 6,152,364 A | 11/2000 | Schoonen et al. |
| 6,154,668 A | 11/2000 | Pedersen et al. |
| 6,154,726 A | 11/2000 | Rensimer et al. |
| 6,157,914 A | 12/2000 | Seto et al. |
| 6,158,965 A | 12/2000 | Butterfield et al. |
| 6,160,478 A | 12/2000 | Jacobsen et al. |
| 6,161,095 A | 12/2000 | Brown |
| 6,161,141 A | 12/2000 | Dillon |
| 6,163,737 A | 12/2000 | Fedor et al. |
| 6,165,154 A | 12/2000 | Gray et al. |
| 6,168,563 B1 | 1/2001 | Brown |
| 6,170,007 B1 | 1/2001 | Venkatraman et al. |
| 6,170,746 B1 | 1/2001 | Brook et al. |
| 6,171,112 B1 | 1/2001 | Clark et al. |
| 6,171,237 B1 | 1/2001 | Avitall et al. |
| 6,171,264 B1 | 1/2001 | Bader |
| 6,173,198 B1 | 1/2001 | Schulze et al. |
| 6,175,779 B1 | 1/2001 | Barrett |
| 6,175,977 B1 | 1/2001 | Schumacher et al. |
| 6,176,392 B1 | 1/2001 | William et al. |
| 6,182,047 B1 | 1/2001 | Dirbas |
| 6,183,417 B1 | 2/2001 | Geheb et al. |

(56) References Cited

U.S. PATENT DOCUMENTS

| | | |
|---|---|---|
| 6,186,145 B1 | 2/2001 | Brown |
| 6,192,320 B1 | 2/2001 | Margrey et al. |
| 6,193,480 B1 | 2/2001 | Butterfield |
| 6,195,887 B1 | 3/2001 | Danby et al. |
| 6,198,394 B1 | 3/2001 | Jacobsen et al. |
| 6,200,264 B1 | 3/2001 | Satherley et al. |
| 6,200,289 B1 | 3/2001 | Hochman et al. |
| 6,202,923 B1 | 3/2001 | Boyer et al. |
| 6,203,495 B1 | 3/2001 | Bardy |
| 6,203,528 B1 | 3/2001 | Deckert et al. |
| 6,206,238 B1 | 3/2001 | Ophardt |
| 6,206,829 B1 | 3/2001 | Iliff |
| 6,210,361 B1 | 4/2001 | Kamen et al. |
| 6,213,391 B1 | 4/2001 | Lewis |
| 6,213,738 B1 | 4/2001 | Danby et al. |
| 6,219,439 B1 | 4/2001 | Burger |
| 6,219,587 B1 | 4/2001 | Ahlin et al. |
| 6,221,011 B1 | 4/2001 | Bardy |
| 6,221,012 B1 | 4/2001 | Maschke et al. |
| 6,222,619 B1 | 4/2001 | Herron et al. |
| 6,224,549 B1 | 5/2001 | Drongelen |
| 6,225,901 B1 | 5/2001 | Kail, IV |
| 6,226,564 B1 | 5/2001 | Stuart |
| 6,226,745 B1 | 5/2001 | Wiederhold |
| 6,230,927 B1 | 5/2001 | Schoonen et al. |
| 6,234,997 B1 | 5/2001 | Kamen et al. |
| 6,245,013 B1 | 6/2001 | Minoz et al. |
| 6,246,473 B1 | 6/2001 | Smith, Jr. et al. |
| 6,248,063 B1 | 6/2001 | Barnhill et al. |
| 6,248,065 B1 | 6/2001 | Brown |
| 6,255,951 B1 | 7/2001 | De La Huerga |
| 6,256,643 B1 | 7/2001 | Cork et al. |
| 6,256,967 B1 | 7/2001 | Hebron et al. |
| 6,259,355 B1 | 7/2001 | Chaco et al. |
| 6,259,654 B1 | 7/2001 | De La Huerga |
| 6,266,645 B1 | 7/2001 | Simpson |
| 6,269,340 B1 | 7/2001 | Ford et al. |
| D446,854 S | 8/2001 | Cheney, II et al. |
| 6,270,455 B1 | 8/2001 | Brown |
| 6,270,457 B1 | 8/2001 | Bardy |
| 6,272,394 B1 | 8/2001 | Lipps |
| 6,272,505 B1 | 8/2001 | De La Huerga |
| 6,277,072 B1 | 8/2001 | Bardy |
| 6,283,322 B1 | 9/2001 | Liff et al. |
| 6,283,944 B1 | 9/2001 | McMullen et al. |
| 6,290,646 B1 | 9/2001 | Cosentino et al. |
| 6,290,650 B1 | 9/2001 | Butterfield et al. |
| 6,294,999 B1 | 9/2001 | Yarin et al. |
| 6,295,506 B1 | 9/2001 | Heinonen |
| 6,304,788 B1 | 10/2001 | Eady et al. |
| 6,306,088 B1 | 10/2001 | Krausman et al. |
| 6,307,956 B1 | 10/2001 | Black |
| 6,308,171 B1 | 10/2001 | De La Huerga |
| 6,311,163 B1 | 10/2001 | Sheehan et al. |
| 6,312,227 B1 | 11/2001 | Davis |
| 6,312,378 B1 | 11/2001 | Bardy |
| 6,314,384 B1 | 11/2001 | Goetz |
| 6,317,719 B1 | 11/2001 | Schrier et al. |
| 6,319,200 B1 | 11/2001 | Lai et al. |
| 6,321,203 B1 | 11/2001 | Kameda |
| 6,322,504 B1 | 11/2001 | Kirshner |
| 6,322,515 B1 | 11/2001 | Goor et al. |
| 6,330,491 B1 | 12/2001 | Lion |
| RE37,531 E | 1/2002 | Chaco et al. |
| 6,337,631 B1 | 1/2002 | Pai et al. |
| 6,338,007 B1 | 1/2002 | Broadfield et al. |
| 6,339,732 B1 | 1/2002 | Phoon et al. |
| 6,345,260 B1 | 2/2002 | Cummings, Jr. et al. |
| 6,346,886 B1 | 2/2002 | De La Huerga |
| 6,352,200 B1 | 3/2002 | Schoonen et al. |
| 6,353,817 B1 | 3/2002 | Jacobs et al. |
| 6,358,225 B1 | 3/2002 | Butterfield |
| 6,358,237 B1 | 3/2002 | Paukovits et al. |
| 6,361,263 B1 | 3/2002 | Dewey et al. |
| 6,362,591 B1 | 3/2002 | Moberg |
| 6,363,282 B1 | 3/2002 | Nichols et al. |
| 6,363,290 B1 | 3/2002 | Lyle et al. |
| 6,364,834 B1 | 4/2002 | Reuss et al. |
| 6,368,273 B1 | 4/2002 | Brown |
| 6,370,841 B1 | 4/2002 | Chudy et al. |
| 6,381,577 B1 | 4/2002 | Brown |
| 6,385,505 B1 | 5/2002 | Lipps |
| 6,393,369 B1 | 5/2002 | Carr |
| 6,397,190 B1 | 5/2002 | Goetz |
| 6,402,702 B1 | 6/2002 | Gilcher et al. |
| 6,406,426 B1 | 6/2002 | Reuss et al. |
| 6,407,335 B1 | 6/2002 | Franklin-Lees et al. |
| 6,408,330 B1 | 6/2002 | DeLaHuerga |
| 6,416,471 B1 | 7/2002 | Kumar et al. |
| 6,421,650 B1 | 7/2002 | Goetz et al. |
| 6,427,088 B1 | 7/2002 | Bowman, IV et al. |
| 6,434,531 B1 | 8/2002 | Lancelot et al. |
| 6,434,569 B1 | 8/2002 | Tomlinson et al. |
| 6,438,451 B1 | 8/2002 | Lion |
| RE37,829 E | 9/2002 | Charhut et al. |
| 6,449,927 B2 | 9/2002 | Hebron et al. |
| 6,450,956 B1 | 9/2002 | Rappaport et al. |
| 6,458,102 B1 | 10/2002 | Mann et al. |
| 6,468,242 B1 | 10/2002 | Wilson et al. |
| 6,470,234 B1 | 10/2002 | McGrady |
| 6,471,089 B2 | 10/2002 | Liff et al. |
| 6,471,645 B1 | 10/2002 | Warkentin et al. |
| 6,475,146 B1 | 11/2002 | Frelburger et al. |
| 6,475,148 B1 | 11/2002 | Jackson et al. |
| 6,475,180 B2 | 11/2002 | Peterson et al. |
| 6,478,737 B2 | 11/2002 | Bardy |
| 6,485,465 B2 | 11/2002 | Moberg et al. |
| 6,511,138 B1 | 1/2003 | Gardner et al. |
| 6,519,569 B1 | 2/2003 | White et al. |
| 6,537,244 B2 | 3/2003 | Paukovits |
| 6,542,902 B2 | 4/2003 | Dulong et al. |
| 6,542,910 B2 | 4/2003 | Cork et al. |
| 6,544,174 B2 | 4/2003 | West et al. |
| 6,544,228 B1 | 4/2003 | Heitmeier |
| 6,551,243 B2 | 4/2003 | Bocionek et al. |
| 6,551,276 B1 | 4/2003 | Mann et al. |
| 6,554,791 B1 | 4/2003 | Cartledge et al. |
| 6,554,798 B1 | 4/2003 | Mann et al. |
| 6,555,986 B2 | 4/2003 | Moberg |
| 6,558,321 B1 | 5/2003 | Burd et al. |
| 6,561,975 B1 | 5/2003 | Pool et al. |
| 6,562,001 B2 | 5/2003 | Lebel et al. |
| 6,564,104 B2 | 5/2003 | Nelson et al. |
| 6,564,105 B2 | 5/2003 | Starkweather et al. |
| 6,564,121 B1 | 5/2003 | Wallace et al. |
| 6,571,128 B2 | 5/2003 | Lebel et al. |
| 6,575,900 B1 | 6/2003 | Zweig et al. |
| 6,577,899 B2 | 6/2003 | Lebel et al. |
| 6,579,232 B2 | 6/2003 | Sakamaki et al. |
| 6,581,069 B1 | 6/2003 | Robinson et al. |
| 6,581,798 B2 | 6/2003 | Liff et al. |
| 6,584,336 B1 | 6/2003 | Ali et al. |
| 6,585,157 B2 | 7/2003 | Brandt et al. |
| 6,585,644 B2 | 7/2003 | Lebel et al. |
| 6,585,675 B1 | 7/2003 | O'Mahony et al. |
| 6,592,551 B1 | 7/2003 | Cobb |
| 6,593,528 B2 | 7/2003 | Franklin-Lees et al. |
| 6,607,485 B2 | 8/2003 | Bardy |
| 6,610,973 B1 | 8/2003 | Davis, III |
| 6,613,009 B1 | 9/2003 | Bainbridge et al. |
| 6,635,014 B2 | 10/2003 | Starkweather et al. |
| 6,648,821 B2 | 11/2003 | Lebel et al. |
| 6,659,948 B2 | 12/2003 | Lebel et al. |
| 6,664,893 B1 | 12/2003 | Eveland et al. |
| 6,668,196 B1 | 12/2003 | Villegas et al. |
| 6,673,314 B1 | 1/2004 | Burbank et al. |
| 6,687,546 B2 | 2/2004 | Lebel et al. |
| 6,689,091 B2 | 2/2004 | Bui et al. |
| 6,694,191 B2 | 2/2004 | Starkweather et al. |
| 6,694,334 B2 | 2/2004 | DuLong et al. |
| 6,711,460 B1 | 3/2004 | Reese |
| 6,731,324 B2 | 5/2004 | Levy |
| 6,733,447 B2 | 5/2004 | Lai et al. |
| 6,735,497 B2 | 5/2004 | Wallace et al. |

(56) References Cited

U.S. PATENT DOCUMENTS

| | | | |
|---|---|---|---|
| 6,740,075 | B2 | 5/2004 | Lebel et al. |
| 6,746,398 | B2 | 6/2004 | Hervy et al. |
| 6,758,810 | B2 | 7/2004 | Lebel et al. |
| 6,768,425 | B2 | 7/2004 | Flaherty et al. |
| 6,771,369 | B2 | 8/2004 | Rzasa et al. |
| 6,775,602 | B2 | 8/2004 | Gordon, Jr. et al. |
| 6,776,304 | B2 | 8/2004 | Liff et al. |
| 6,790,198 | B1 | 9/2004 | White et al. |
| 6,804,656 | B1 | 10/2004 | Rosenfeld et al. |
| 6,810,290 | B2 | 10/2004 | Lebel et al. |
| 6,811,533 | B2 | 11/2004 | Lebel et al. |
| 6,811,534 | B2 | 11/2004 | Bowman, IV et al. |
| 6,811,707 | B2 | 11/2004 | Rovatti et al. |
| 6,813,473 | B1 | 11/2004 | Bruker |
| 6,813,519 | B2 | 11/2004 | Lebel et al. |
| 6,814,255 | B2 | 11/2004 | Liff et al. |
| 6,820,093 | B2 | 11/2004 | De La Huerga |
| 6,842,736 | B1 | 1/2005 | Brzozowski |
| 6,847,861 | B2 | 1/2005 | Lunak et al. |
| 6,854,088 | B2 | 2/2005 | Massengale et al. |
| 6,871,211 | B2 | 3/2005 | Labounty et al. |
| 6,873,268 | B2 | 3/2005 | Lebel et al. |
| 6,877,530 | B2 | 4/2005 | Osborne et al. |
| 6,880,034 | B2 | 4/2005 | Manke et al. |
| 6,885,288 | B2 | 4/2005 | Pincus |
| 6,892,941 | B2 | 5/2005 | Rosenblum |
| 6,912,549 | B2 | 6/2005 | Rotter et al. |
| 6,913,590 | B2 | 7/2005 | Sorenson et al. |
| 6,915,823 | B2 | 7/2005 | Osborne et al. |
| 6,928,452 | B2 | 8/2005 | De La Huerga |
| 6,950,708 | B2 | 9/2005 | Bowman, IV et al. |
| 6,958,705 | B2 | 10/2005 | Lebel et al. |
| 6,974,437 | B2 | 12/2005 | Lebel et al. |
| 6,975,924 | B2 | 12/2005 | Kircher et al. |
| 6,976,628 | B2 | 12/2005 | Krupa |
| 6,979,306 | B2 | 12/2005 | Moll |
| 6,980,958 | B1 | 12/2005 | Surwit et al. |
| 6,981,644 | B2 | 1/2006 | Cheong et al. |
| 6,985,870 | B2 | 1/2006 | Martucci et al. |
| 6,991,002 | B2 | 1/2006 | Osborne et al. |
| 6,995,664 | B1 | 2/2006 | Darling |
| 7,006,893 | B2 | 2/2006 | Hart et al. |
| 7,015,806 | B2 | 3/2006 | Naidoo et al. |
| 7,017,622 | B2 | 3/2006 | Osborne et al. |
| 7,017,623 | B2 | 3/2006 | Tribble et al. |
| 7,028,723 | B1 | 4/2006 | Alouani et al. |
| 7,096,212 | B2 | 8/2006 | Tribble et al. |
| 7,117,902 | B2 | 10/2006 | Osborne |
| 7,151,982 | B2 | 12/2006 | Liff et al. |
| 7,194,336 | B2 | 3/2007 | DiGianfilippo et al. |
| 7,209,891 | B1 | 4/2007 | Addy et al. |
| 7,240,699 | B2 | 7/2007 | Osborne et al. |
| 7,277,579 | B2 | 10/2007 | Lee et al. |
| 7,277,757 | B2 | 10/2007 | Casavant et al. |
| 7,317,967 | B2 | 1/2008 | DiGianfilippo et al. |
| 7,343,224 | B2 | 3/2008 | DiGianfilippo et al. |
| 7,403,901 | B1 | 7/2008 | Carley et al. |
| 7,427,002 | B2 | 9/2008 | Liff et al. |
| 7,493,263 | B2 | 2/2009 | Helmus et al. |
| 7,499,581 | B2 | 3/2009 | Tribble et al. |
| 7,555,557 | B2 | 6/2009 | Bradley et al. |
| 7,561,312 | B1 | 7/2009 | Proudfoot et al. |
| 7,581,953 | B2 | 9/2009 | Lehmann et al. |
| 7,599,516 | B2 | 10/2009 | Limer et al. |
| 7,610,115 | B2 | 10/2009 | Rob et al. |
| 7,630,908 | B1 | 12/2009 | Amrien et al. |
| 7,636,718 | B1 | 12/2009 | Steen et al. |
| 7,672,859 | B1 | 3/2010 | Louie et al. |
| 7,698,019 | B2 | 4/2010 | Moncrief et al. |
| 7,734,478 | B2 | 6/2010 | Goodall et al. |
| 7,753,085 | B2 | 7/2010 | Tribble et al. |
| 7,769,601 | B1 | 8/2010 | Bleser et al. |
| 7,783,383 | B2 | 8/2010 | Eliuk et al. |
| D624,225 | S | 9/2010 | Federico et al. |
| 7,801,642 | B2 | 9/2010 | Ansari et al. |
| 7,847,970 | B1 | 12/2010 | McGrady |
| 7,853,621 | B2 | 12/2010 | Guo |
| 7,931,859 | B2 | 4/2011 | Mlodzinski et al. |
| 7,937,290 | B2 | 5/2011 | Bahir |
| 7,986,369 | B1 | 7/2011 | Burns |
| 7,991,507 | B2 | 8/2011 | Liff et al. |
| 8,170,271 | B2 | 5/2012 | Chen |
| 8,191,339 | B2 | 6/2012 | Tribble et al. |
| 8,215,557 | B1 | 7/2012 | Reno et al. |
| 8,220,503 | B2 | 7/2012 | Tribble et al. |
| 8,225,824 | B2 | 7/2012 | Eliuk et al. |
| D667,961 | S | 9/2012 | Marmier |
| 8,267,129 | B2 | 9/2012 | Doherty et al. |
| 8,271,138 | B2 | 9/2012 | Eliuk et al. |
| 8,280,549 | B2 | 10/2012 | Liff et al. |
| 8,284,305 | B2 | 10/2012 | Newcomb et al. |
| 8,308,414 | B2 | 11/2012 | Schifman et al. |
| 8,374,887 | B1 | 2/2013 | Alexander |
| 8,386,070 | B2 | 2/2013 | Eliuk et al. |
| 8,548,824 | B1 | 10/2013 | daCosta |
| 8,554,579 | B2 | 10/2013 | Tribble et al. |
| D693,480 | S | 11/2013 | Spiess et al. |
| 8,595,206 | B1 | 11/2013 | Ansari |
| 8,666,541 | B1 | 3/2014 | Ansari et al. |
| 8,678,047 | B2 | 3/2014 | Tribble et al. |
| D715,958 | S | 10/2014 | Bossart et al. |
| 9,053,218 | B2 | 6/2015 | Osborne et al. |
| D733,480 | S | 7/2015 | Shao |
| D738,152 | S | 9/2015 | Grasselli et al. |
| D753,428 | S | 4/2016 | Shao |
| 9,355,273 | B2 | 5/2016 | Stevens et al. |
| 9,362,969 | B1 | 6/2016 | Burgess et al. |
| 9,382,021 | B2 | 7/2016 | Tribble et al. |
| 9,662,273 | B2 | 5/2017 | Ranalletta et al. |
| 9,930,297 | B2 | 3/2018 | Alexander et al. |
| 9,956,145 | B2 | 5/2018 | Thompson et al. |
| 2006/0200369 | A1 | 9/2006 | Batch et al. |
| 2007/0192139 | A1 | 8/2007 | Cookson et al. |
| 2008/0046292 | A1* | 2/2008 | Myers .................. G06F 16/283 705/3 |
| 2008/0147554 | A1* | 6/2008 | Stevens .................. G16H 10/60 705/51 |
| 2010/0324936 | A1 | 12/2010 | Vishnubhatla et al. |
| 2013/0197930 | A1 | 8/2013 | Garibaldi et al. |
| 2013/0304510 | A1 | 11/2013 | Chen et al. |
| 2014/0136237 | A1 | 5/2014 | Anderson et al. |
| 2014/0156294 | A1 | 6/2014 | Tribble et al. |
| 2015/0149208 | A1* | 5/2015 | Lynch .................. G16H 10/60 705/3 |

FOREIGN PATENT DOCUMENTS

| | | |
|---|---|---|
| CN | 1131076 | 12/2003 |
| EP | 0237588 | 9/1987 |
| EP | 0462466 | 12/1991 |
| EP | 0505627 | 9/1992 |
| EP | 0522527 | 1/1993 |
| EP | 0439355 | 9/1994 |
| EP | 0844581 | 5/1998 |
| EP | 0960627 | 12/1999 |
| EP | 0970655 | 1/2000 |
| EP | 1107158 A1 | 6/2001 |
| EP | 1097671 | 2/2003 |
| EP | 1939785 A2 | 7/2008 |
| EP | 3161778 | 5/2017 |
| GB | 994977 A | 6/1965 |
| GB | 2210713 | 2/1987 |
| GB | 2279784 | 1/1995 |
| GB | 2285135 | 6/1995 |
| GB | 2379037 | 2/2003 |
| JP | 3423055 B2 | 1/1994 |
| JP | 07204253 A | 8/1995 |
| JP | 2000036032 A | 2/2000 |
| JP | 2002011095 | 1/2002 |
| JP | 2002092181 A | 3/2002 |
| JP | 2002520718 | 7/2002 |
| JP | 2003022322 | 1/2003 |
| JP | 2004078970 | 3/2004 |
| JP | 2004326436 | 11/2004 |

US 12,658,315 B2 body

(56) References Cited

FOREIGN PATENT DOCUMENTS

| | | | |
|---|---|---|---|
| JP | 2004340770 | A | 12/2004 |
| JP | 2005252710 | A | 9/2005 |
| JP | 2006033291 | A | 2/2006 |
| JP | 2006334062 | | 12/2006 |
| JP | 2007198934 | A | 8/2007 |
| JP | 2008139201 | A | 6/2008 |
| JP | 4276654 | B2 | 6/2009 |
| JP | 2009265827 | A | 11/2009 |
| JP | 2010056619 | A | 3/2010 |
| JP | 2010170504 | A | 8/2010 |
| JP | 2010533927 | A | 10/2010 |
| JP | 2011151430 | A | 8/2011 |
| JP | 2012078265 | | 4/2012 |
| JP | 5342197 | B2 | 11/2013 |
| JP | 5747150 | B2 | 7/2015 |
| JP | 6086813 | | 3/2017 |
| KR | 20000036642 | | 7/2000 |
| KR | 1020000036642 | | 7/2000 |
| KR | 20010094703 | A | 11/2001 |
| KR | 1020010094703 | | 11/2001 |
| KR | 20050054379 | | 12/2003 |
| KR | 20110115927 | A | 10/2011 |
| KR | 1020110115927 | | 10/2011 |
| KR | 10-2013-0001500 | | 1/2013 |
| KR | 10-2013-0001539 | | 1/2013 |
| KR | 20130001500 | | 1/2013 |
| WO | WO8400493 | | 2/1984 |
| WO | WO9524010 | A1 | 9/1995 |
| WO | WO9634291 | A1 | 10/1996 |
| WO | WO9741525 | | 11/1997 |
| WO | WO9814275 | A1 | 4/1998 |
| WO | WO9815092 | A1 | 4/1998 |
| WO | WO9824358 | A1 | 6/1998 |
| WO | WO9833433 | A1 | 8/1998 |
| WO | WO9859487 | | 12/1998 |
| WO | WO9904043 | | 1/1999 |
| WO | WO9910029 | | 3/1999 |
| WO | WO9942933 | | 8/1999 |
| WO | WO9944162 | | 9/1999 |
| WO | WO9959472 | | 11/1999 |
| WO | WO0013588 | | 3/2000 |
| WO | WO0029983 | | 5/2000 |
| WO | WO0043941 | | 7/2000 |
| WO | WO0052437 | | 9/2000 |
| WO | WO0052626 | | 9/2000 |
| WO | WO0057339 | | 9/2000 |
| WO | WO0060449 | | 10/2000 |
| WO | WO0069331 | | 11/2000 |
| WO | WO0072181 | | 11/2000 |
| WO | WO0078374 | | 12/2000 |
| WO | WO0101305 | | 1/2001 |
| WO | WO0102979 | | 1/2001 |
| WO | WO0106468 | | 1/2001 |
| WO | WO0145774 | | 6/2001 |
| WO | WO0217777 | | 7/2002 |
| WO | WO02091276 | A1 | 11/2002 |
| WO | WO03025826 | A2 | 3/2003 |
| WO | WO03094073 | | 11/2003 |
| WO | WO2004070557 | | 8/2004 |
| WO | WO2004070994 | | 8/2004 |
| WO | 2016003902 | | 1/2016 |

OTHER PUBLICATIONS

Extended European Search Report for related European Application No. 20203335.3; report dated Apr. 23, 2021; (15 pages).
Extended European Search Report for related European Application No. 15815359.3; mailed Dec. 2, 2018 (9 bages).
Singapore Written Opinion for related Singapore Application No. 11201610717W, opinion dated Aug. 14, 2018 (6 pages).
Japanese Office Action and English translation for related Japanese Application No. 2016-575743; action dated May 21, 2019 (13 pages).
Examination Report for related Australian Application No. 2015284368; action dated Feb. 20, 2020 (6 pages).
Japanese Office Action and English translation for related Japanese Application No. 2016-575743; action dated Mar. 31, 2020 (5 pages).
Australian Examination Report for corresponding AU Patent Application No. 2015284368, mailed Jan. 21, 2021.
Examination Report for related New Zealand Application No. 727697; report dated May 5, 2021; (4 pages).
Canadian Office action for related Canadian application No. 2,953,392; action dated Jul. 7, 2021; (5 pages).
Japanese Office Action for related Japanese Application No. 2020-130857; action dated Oct. 19, 2021; (13 pages).
Examination Report for related New Zealand Application No. 727697; report dated Nov. 29, 2021; (8 pages).
Examination Report for related Australian Application No. 2021201053; action dated Mar. 1, 2022; (6 pages).
Tsao et al., "Decentralized Automated Dispensing Devices: Systematic Review of Clinical and Economic Impacts in Hospitals", The Canadian Journal of Hospital Pharmacy (2014), 67(2), pp. 138-148.
Australian Examination Report No. 1 from corresponding Australian Patent Application No. 2023201223, dated Nov. 4, 2024. 9 pages.

* cited by examiner

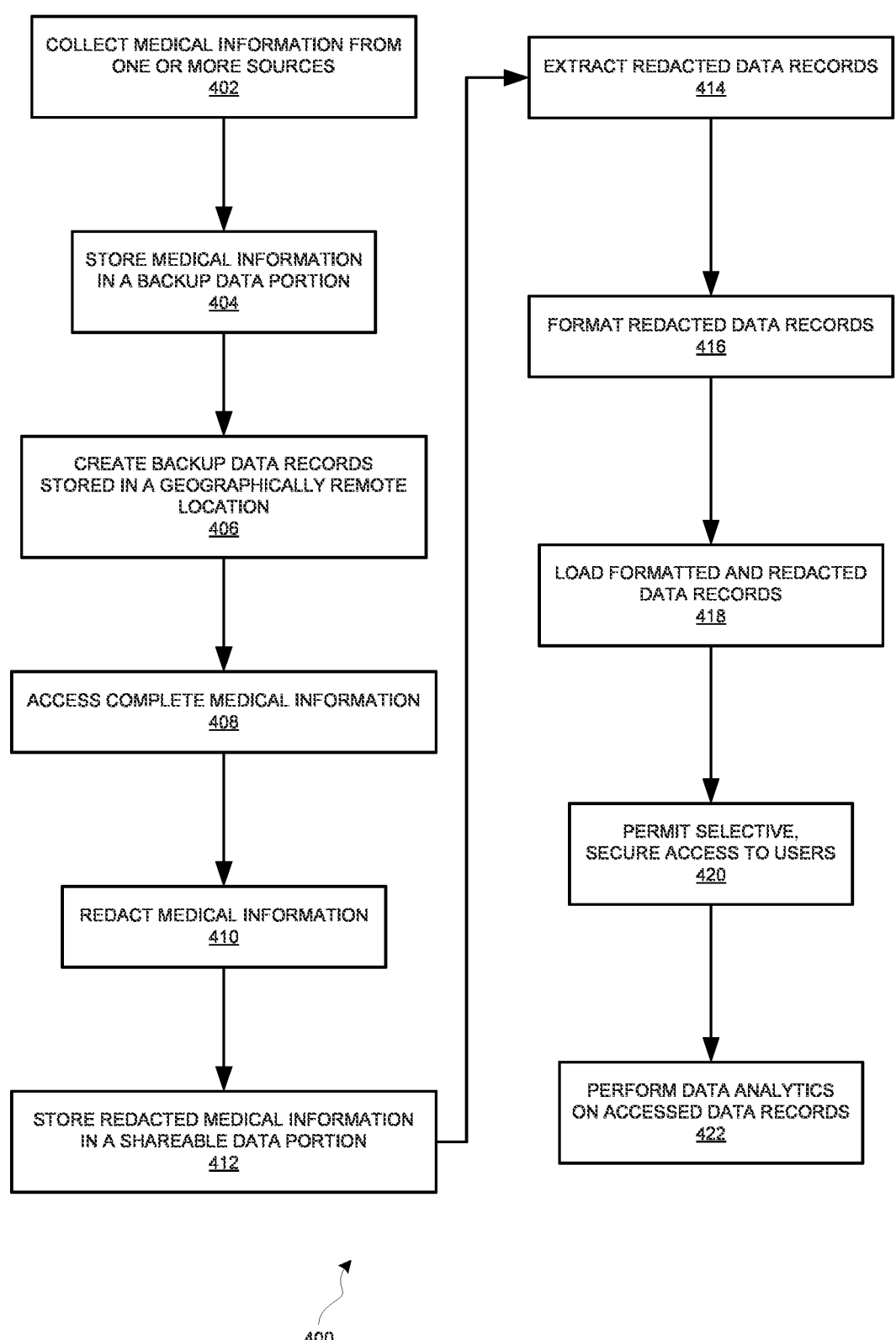

COLLECT MEDICAL INFORMATION FROM
ONE OR MORE SOURCES
402

STORE MEDICAL INFORMATION
IN A BACKUP DATA PORTION
404

CREATE BACKUP DATA RECORDS
STORED IN A GEOGRAPHICALLY REMOTE
LOCATION
406

ACCESS COMPLETE MEDICAL INFORMATION
408

REDACT MEDICAL INFORMATION
410

STORE REDACTED MEDICAL INFORMATION
IN A SHAREABLE DATA PORTION
412

EXTRACT REDACTED DATA RECORDS
414

FORMAT REDACTED DATA RECORDS
416

LOAD FORMATTED AND REDACTED
DATA RECORDS
418

PERMIT SELECTIVE,
SECURE ACCESS TO USERS
420

PERFORM DATA ANALYTICS
ON ACCESSED DATA RECORDS
422

MANAGED MEDICAL INFORMATION EXCHANGE

PRIORITY CLAIM

This application claims priority to and the benefit as a continuation application of U.S. patent application Ser. No. 14/753,712, filed on Jun. 29, 2015, entitled "MANAGED MEDICAL INFORMATION EXCHANGE", now U.S. Pat. No. 11,367,533, which claims priority to U.S. Provisional Application No. 62/019,227, filed on Jun. 30, 2014, entitled "MANAGED MEDICAL INFORMATION EXCHANGE", the entire contents each of which are incorporated herein by reference and relied upon.

BACKGROUND

Many healthcare facilities utilize pharmacy resources to prepare medication preparations that are to be administered to a patient. Such pharmacy resources may be located locally at the healthcare facility or may be remote from the healthcare facility. In either regard, medication preparations at the pharmacy resource may be prepared in response to receipt of a medication dose order. Such medication dose orders may be, in at least some instances, patient-specific dose orders that are generated by a healthcare professional and correspond to a request for preparation of the medication preparation to be prepared for administration to the patient. In other applications, the dose orders may be stock orders or non-patient-specific.

Many healthcare facilities generate records corresponding to dose orders that are prepared by a pharmacy resource. The records may include information received with the medical dose order and/or information that may be added to the record by the pharmacy resource (e.g., including details about the products and/or preparation used to prepare the dose corresponding to the medical dose order). Such records may be stored and/or used locally at the pharmacy resource for a variety of potential purposes including for example, regulatory compliance, patient safety, inventory management, staffing decisions, or other purposes related to the management of the pharmacy resource and/or medication preparations.

Furthermore, continued developments in communication technology and collaborative tools increasingly make it easier to share and access data in a networked environment (e.g., through software services, data sharing platforms, or other network connectivity sometimes collectively referred to as "cloud services"). However, medical information (e.g., including dose order records or the like) may be subjected to access and/or dissemination restrictions. For example, access to such data may be limited to access by appropriate personnel at the healthcare facility or pharmacy resource. For instance, in the United States the Health Insurance Portability and Accountability Act (HIPAA) provides regulatory requirements regarding the handling, dissemination, or other privacy related aspects of medical records that may contain protected health information (PHI). In this regard, the use, dissemination, and/or access to dose order records, and especially patient-specific dose order records that may include PHI may be limited by regulatory compliance and/or other privacy concerns. As such, despite the benefits that may be provided with the ability to collaboratively share data for application of cloud services thereto, limits on the use of data may limit the access to such valuable data.

Furthermore, systems used to maintain and/or generate medical information may be proprietary, such that specific data formats are utilized. Thus data exchange may be limited by data formatting limitations. For instance, data generated or stored in a proprietary format specific to a first entity may not be readable by another entity.

SUMMARY

The present disclosure relates to systems and methods that facilitate collaborative approaches to the management of information, particularly, information related to medication preparation information received in relation to provision of medical care. In this regard, the present disclosure relates to managed exchange of medical information. The exchange of medical information may be improved by use of selective redaction and/or formatting of the medical information. For example, to allow for increased exchange of medical information that may include patient identifying information or protected health information (PHI), certain data of the medical information may be redacted. Furthermore, a cryptographic hash function may be applied that reliably transforms a portion of information (e.g., information related to patient identifier) into a non-identifying value. In turn, records may still be associated with a given patient while the patient's PHI and/or patient identifying information may be removed.

Furthermore, given the potentially wide array of data analytics that may be applied to medical information exchanged using the description presented herein, the data may be formatted prior to access by users of a data exchange platform to facilitate specific data analytics. This may include a standardized format that is common to all users of the system and/or particularized formats corresponding to particular users, particular uses of the data, and/or particular types of data. In any regard, the use of an exchange platform as described herein may facilitate improved access to data to allow for more expanded, robust, and efficient data analytics in a number of contexts. In particular, inter-party exchange of data may be improved through data formatting rules associated with a collaboration system described herein. As such, data analytics may be expanded as data from a plurality of sources may be utilized and provided in a format. For example, data analytics related to multiple, inter-party data sources may be facilitated by the disclosure presented herein may help improve patient safety (e.g., by identifying potentially harmful trends with a collection of data), provide business intelligence, assist in reducing the cost of healthcare, or other meaningful benefits.

Accordingly, a first aspect includes a system for exchange of information related to patient-specific medication preparations. The system includes a data storage device in operative communication with one or more healthcare facilities to receive, from the one or more healthcare facilities, information regarding patient-specific medication preparations prepared at corresponding respective ones of the one or more healthcare facilities. In embodiments, the medical information may also include non-patient specific data received from one or more additional sources. The data storage device includes a sharable data portion that stores redacted data records having patient identifying (e.g., protected health information (PHI)) removed therefrom. The redacted records correspond to the information regarding medication preparations that is received from the one or more healthcare facilities. The system also includes a collaboration module that is in operative communication with the data storage device. The collaboration module is operative to access the shareable data portion to extract data from the shareable data portion, transform the extracted data into a data format based at least in part on a predetermined operational need, and load the formatted data into a remotely accessible data storage location that is accessible remotely from the data storage device. In this regard, the predetermined operational need may be based on an identified data analysis to be performed, an identity of a party accessing the data, a requested format by a party accessing the data, or some other particular purpose for the data.

A number of feature refinements and additional features are applicable to the first aspect. These feature refinements and additional features may be used individually or in any combination. As such, each of the following features that will be discussed may be, but are not required to be, used with any other feature or combination of features of the first aspect.

For example, the PHI may include a patient identifier. Furthermore, the system of the first aspect may facilitate removal of patient identifying information, while still allowing an association between data records and a given patient. As such, one or more of the redacted data records stored in the shareable data portion may also comprise a unique identifier that associates one or more portions of the information regarding medication preparations to a given patient without providing identifying characteristics relative to the patient. The unique identifier may include a hash value generated in response to application of a hash function to the patient identifier.

The hash function may be executed by a processor at the data storage device to generate the redacted data records that are stored in the shareable data portion. Alternatively, a hash function may be executed locally at the one or more healthcare facilities to remove patient identifying information prior to providing the data to the data storage device. Accordingly, the system may receive medical information that has been redacted at a data source. As such, the hash function may be executed by a processor at the one or more healthcare facilities to generate the redacted data records that are received at the central storage server for storage in the sharable data portion. In an embodiment, the hash value may include a deterministic, non-invertable value based on the patient identifier. That is, for each given unique patient identifier used to generate a has value, a corresponding unique hash value is generated. Furthermore, a user may not be able to ascertain the plain text patient identifier using only the hash function.

In an embodiment, the data storage device may also include a backup data portion that comprises complete data records (i.e., that potentially includes PHI) corresponding to at least a portion of the information regarding medication preparations received from the one or more healthcare facilities. The backup data portion and the shareable data portion may be separately accessible on the data storage device. That is, users who access the shareable data portion may not have access to the backup data portion. The collaboration module may provide a plurality of users selective and secure access to the shareable data portion based on a plurality of security layers applied to access the shareable data portion.

In an embodiment, the data format in which the collaboration module provides the redacted data may include a standardized data format accessible by the plurality of users. The data format may include a plurality of distinct data formats. As such, different ones of the plurality of distinct data formats may be accessible by corresponding different respective ones of the plurality of users.

In an embodiment, the data storage device may include a data storage server located remotely from the one or more healthcare facilities. Specifically, the data storage device may comprise a plurality of mirrored data servers distributed at distinct geographic locations. As such, redundancy may be provided such that the likelihood of data loss at both of the distributed data servers is reduced.

In an embodiment, the system of the first aspect may be used in connection with the ordering, preparation, and/or administration of a dose to a patient. As such, the information regarding medication preparations may include dose order records generated in response to received dose orders for mediation preparations to be administered to a patient.

The system of the first aspect may also include an analytics module in operative communication with the data storage location to retrieve the formatted data. In turn, the analytics module may be operative to perform at least one analysis on the information regarding medication preparations in relation to a specific given patient without the particular identity of the specific given patient. The analysis performed by the data analytics module may at least include analysis with respect to the unique patient identifier. For instance, doses administered to a given patient may be analyzed.

Other analysis may be facilitated or conducted without limitation. Examples of such analysis may include error tracking in relation to one or more given dose order data fields. Accordingly, tracked errors may be examined to determine if a common data parameter exists to facilitate a root cause investigation. For example, high error rates with respect to doses prepared with a given drug or medical product may allow for underlying causes (e.g., a potential confusing label or the like) to be identified with respect to the given drug or medical product.

Further still, data analysis may be facilitated or performed to help parameterize and evaluate a supply chain related to the manufacture, ordering, preparation, distribution, and/or administration of a dose. In this regard, as data related to a given dose, including medical product information used in the preparation of the dose, may be provided to the system, inventory tracking and supply chain evaluation may be conducted at any one or more portions of the supply chain from, for example, a medical product manufacturer to, for example, dose administration. Such analysis may be at least partially based on one or more dose order data fields contained in the medical information received at the system.

In an embodiment, the information regarding medication preparations may be received at the data storage device in accord with a local data policy of each respective one of the one or more healthcare facilities. As such and as stated above, patient identifying information may be removed from the medical information prior to the receipt of the data at the system of the first aspect. The removal of such patient identifiers may be at least in part based on the local data policy of each respective healthcare facility. The local data policy may be configurable for each respective one of the healthcare-facilities.

A second aspect includes a method for generation of shareable information regarding patient-specific medication preparations. The method includes receiving, from one or more healthcare facilities, information regarding patient-specific medication preparations prepared at corresponding respective ones of the one or more healthcare facilities for administration to a patient. The method further includes storing the information as a shareable data portion stored on a data storage device in the form of redacted data records that correspond to the information regarding patient-specific medication preparations that is received from the one or more healthcare facilities. The redacted records have patient identifying information (e.g., protected healthcare information (PHI)) removed therefrom. The method further includes formatting the redacted data records to a format corresponding with a predetermined operational need and loading the formatted data into a remotely accessible storage location for access by users remote from the storage location.

A number of feature refinements and additional features are applicable to the second aspect. These feature refinements and additional features may be used individually or in any combination. As such, each of the following features that will be discussed may be, but are not required to be, used with any other feature or combination of features of the second aspect. Furthermore, any one or more of the feature refinements and additional features described above in relation to the first aspect may be, but are not required to be, used with the second aspect.

For instance, in an embodiment, the PHI may include at least a patient identifier. The method may further include associating a unique identifier with one or more of the redacted data records that corresponds to a given patient and does not provide identifying capability relative to the patient. As such, the storing may further include applying a hash function to the patient identifier and generating the unique identifier in response to the applying. The unique identifier may, in turn, comprise a hash value resulting from the applying.

In an embodiment, the method may further include providing a plurality of users selective and secure access to the redacted data records. For instance, to access the redacted data records, a user may be required to undergo a plurality of security layers that may require provision of authentication information.

In an embodiment, the formatting may include formatting the redacted data records to a standardized format accessible by the plurality of users. Additionally or alternatively, the formatting may include formatting the redacted data records to a plurality of distinct data formats. The different ones of the plurality of distinct data formats may be accessible by corresponding different respective ones of the plurality of users.

In an embodiment, the method may further include generating the information regarding medication preparations comprise dose order records in response to received dose orders for mediation preparations to be administered to a patient. The method may also include accessing the data storage location to retrieve the formatted data and analyzing the information regarding medication preparations in relation to a specific given patient without the particular identity of the specific given patient. The method may include performing any one or more of the types of analysis described above in relation to the first aspect.

Additionally, the method may further include that the receiving the information regarding medication preparations is at least partially based on a local data policy of each respective one of the one or more healthcare facilities. As such and as described above, a local data policy may be enforced at the healthcare facility.

While the foregoing has referenced receiving medical information from a healthcare facility, the foregoing system and method aspects may also be utilized to receive medical information from any one or more of a plurality of data sources. Such data sources may include pharmaceutical manufacturers that manufacture drug products or medical products (e.g., that may be used in the preparation of a dose). The data sources may also include hospital information systems. Hospital information systems may provide data related to inventory tracking of medical products received and/or distributed throughout a facility. The hospital information systems may also provide medical information including medical records or the like. Additional data sources may include, for example, information from medical device operational databases (e.g., including administration devices such as infusion pumps) and/or dispensing cabinets. Furthermore, any one or more of the data sources may, but are not required to, access data for purposes of performing data analytics or the like. Accordingly, data analytics on aggregated data received from a number of sources may be facilitated. In this regard, data originating from a plurality of sources in connection with the manufacture, ordering, preparation, and/or administration of a dose may be aggregated to provide a wider array of analytical options in relation to the data. The improved access to such aggregated, redacted, and formatted data may facilitate improvements in a number of contexts including patient safety, pharmacy efficiency, business development, inventory management, and others.

BRIEF DESCRIPTION OF THE DRAWINGS

FIG. 4 is a flow chart depicting an embodiment of a method for exchange of information related to medication preparations.

DETAILED DESCRIPTION

Figure 1:
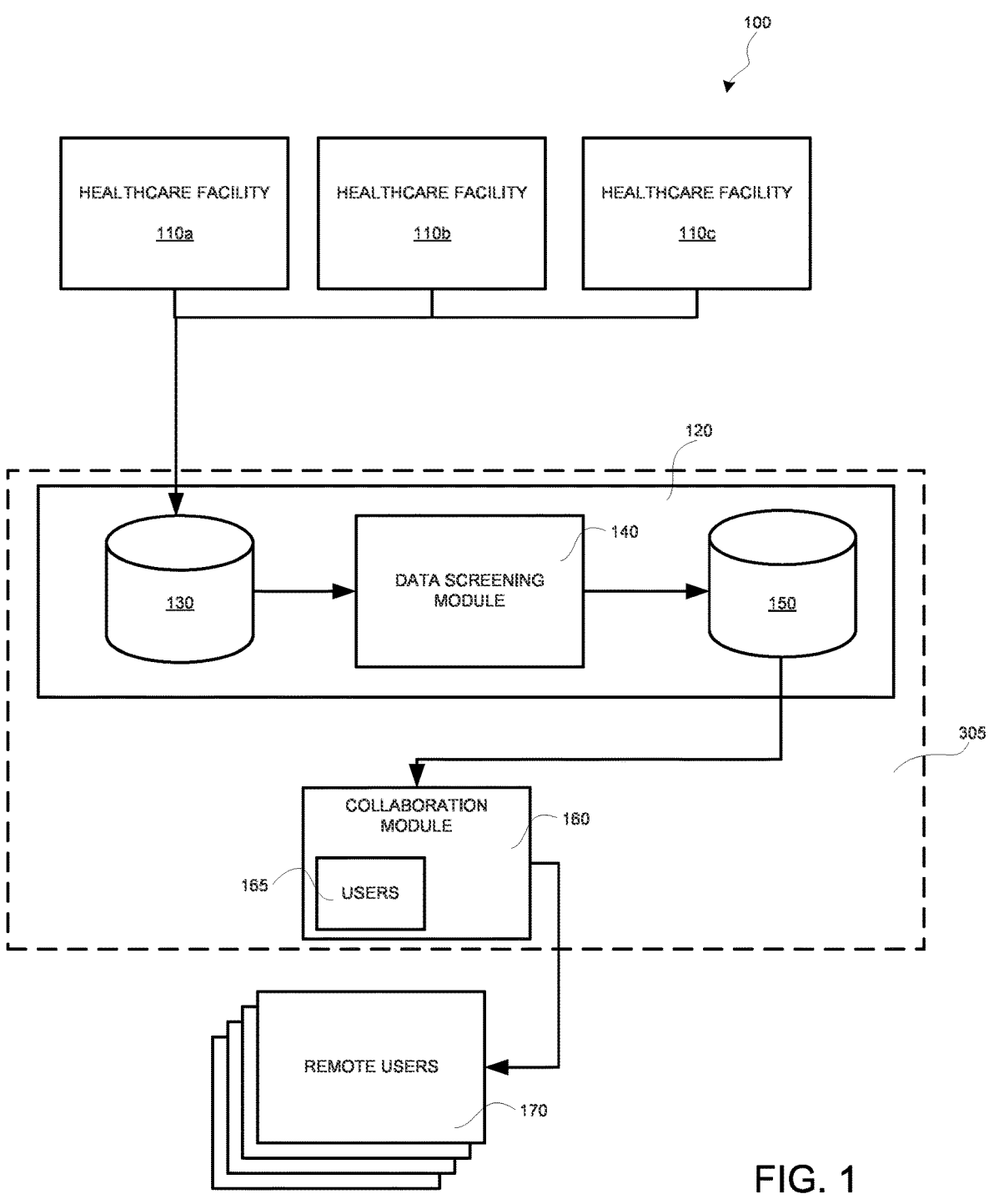
FIG. 1 is a schematic view of an embodiment of a system for exchange of information related to medication preparations.

The following description is not intended to limit the invention to the forms disclosed herein. Consequently, variations and modifications commensurate with the following teachings, skill and knowledge of the relevant art, are within the scope of the present invention. The embodiments described herein are further intended to explain modes known of practicing the invention and to enable others skilled in the art to utilize the invention in such, or other embodiments and with various modifications required by the particular applications(s) or use(s) of the present invention.

The present disclosure generally relates to the exchange of medical information, and especially to the management of the exchange of medical information that may include dose order records related to medication preparations prepared for administration to a patient for the purpose of providing data analytics relative to the medical information. The exchange of such medical information may facilitate a data collaboration platform that enables various entities to perform data analytics on the medical information that may originate from a plurality of data sources for a variety of purposed including, for example, to improve patient safety, to track medical trends, to obtain business intelligence, or for other purposes related to the medical information.

Different entities may have the incentive and/or know-how to provide different kinds of analytics. Accordingly, the present disclosure facilitates a collaboration platform that enables widespread sharing of data to a plurality of parties that may each provide data analytics. In turn, providing a data collaboration platform that provides collected and/or aggregated data in an appropriate format to a plurality of potentially unrelated parties may facilitate improved data analytics based on the variety of providers that may access and/or analyze the formatted data that is provided by the platform.

Accordingly, the platform may be facilitated by a collaboration system that includes at least one data storage device comprising a backup data portion and a shareable data portion. The collaboration system may further include a collaboration module. In this regard, the collaboration system may receive medical information from plurality of data sources. Additionally, the collaboration system may provide access to a plurality of users that access the collaboration system and receive data (e.g., for the purpose of performing data analytics). A party comprising a data source may additionally comprise a party that accesses the collaboration system to access data for the purpose of data analytics. That is, a party (e.g., an individual user, a corporate user, a governmental user, or the like) providing data to the collaboration system may further retrieve data from the collaboration system that includes the data supplied by the party and/or data from other parties that has been aggregated.

A particular concern regarding exchange of medical information includes maintaining the privacy of patients as it relates to the exchange of medical information. For instance, medical information may include patient identifying information (e.g., potentially including protected health information (PHI)). In this regard, dissemination of medical information may subject to restrictions due to regulatory issues (e.g., the Health Insurance Portability and Accountability Act (HIPAA) in the United States may prohibit dissemination of medical information with PHI) or other privacy concerns. Accordingly, the embodiments described herein may be operative to redact medical information to remove patient identifying information (e.g., PHI) from the data.

While removal of PHI or other patient identifying information may be necessary prior to dissemination of medical information for compliance with regulations such as HIPAA or for other privacy factors, it may still be beneficial to associate related medical records to a given patient, even if the identity of a patient is not provided. For instance, if a patient named "Jane Doe" may have a number of medical information records associated with her. The present disclosure facilitates redaction of those medical information records by use of a unique identifier. For instance, Jane Doe's medical records may be associated with "Patient X," where Patient X is non-identifying of Jane Doe. As such, some data analytics may benefit from a non-identifying association between medical records and a given patient (e.g., analytics that relate to trends relative to given patients or analytics that relate to correlations with specific patients). For purposes of these analytics, simply identifying related medical records for a given patient, even in the absence of identifying information regarding the patient may be beneficial. As such, the embodiments described herein may provide such a unique identifier that may associate medical information for a given patient, but not provide any patient identifying information. For instance, a patient identifier may be used as an input to a one-way cryptographic hash function that generates a hash value that may comprise the unique identifier. In this regard, each unique patient identifier may result in a corresponding unique hash value that does not identify the patient when input to the hash function.

As such, the unique identifier (e.g., the hash value) may be used to associate medical information to a given patient without providing patient identification.

As such, a collaboration platform facilitated by the embodiments herein may generate and/or store redacted medical information. A collaboration platform may further provide access to formatted data generated from redacted data records to facilitate data analytics. In turn, the format provided may be a standardized format that is common to all users or may include specialized or particular formats (e.g., proprietary formats) that are based on a user, application, or other criteria. In any regard, the platform described herein including the system and methods described below facilitate improved data sharing to promote application of cloud services and other data analytics to medical information for a variety of purposes.

FIG. 1 depicts an embodiment of a system 100 that facilitates exchange of medical information. In an application, the medical information may include information regarding medication preparations prepared in response to a dose order. For example, a healthcare facility 110 may utilize a local or remote pharmacy resource that is capable of preparing a medication preparation (also referred to herein as a dose) for administration to a patient. In this regard, a plurality of healthcare facilities 110*a*, 110*b*, and 110*c* may be in operative communication with a data storage device 120. While three healthcare facilities 110*a*-110*c* are depicted in FIG. 1, fewer or more healthcare facilities 110 may be in operative communication with the data storage device 120 without limitation.

The healthcare facilities 110*a*-110*c* depicted in FIG. 1 may correspond to any appropriate healthcare facility 110 that generates, stores, supplements, or accesses medical information. Accordingly, the healthcare facilities 110 may include but are not limited to hospitals, pharmacies, outpatient care providers, home care providers, or the like. In any regard, the information provided to the data storage device 120 may include any medical information. In an embodiment, the medical information may relate to medication preparations such as doses to be administered to a patient that are prepared in response to a dose order. In a particular embodiment, the medical information may include patient-specific records corresponding to medication preparations (i.e., doses) that the healthcare facility 110 prepared and/or requested to be prepared for administration to a patient. As such, the healthcare facilities 110 may have access to pharmacy resources that may be utilized to prepare medications for administration to a patient. Access to pharmacy resources may include use of a local pharmacy located at the healthcare facility or use of remote pharmacy that provides medical information (e.g., dose order records) and medication preparations to the healthcare facility 110. For example, at least a portion of the healthcare facilities 110 may include hospital facilities that may include local pharmacy resources that generate dose order records in response to receipt of dose orders that correspond to requested medication preparations.

In this regard, the healthcare facility 110 may utilize a pharmacy workflow manager to generate and/or supplement the medical information that is to be provided to the data storage device 120. This pharmacy workflow manager may include any or all details as described in U.S. application Ser. No. 14/022,415, which is incorporated by reference in its entirety. An example of one such pharmacy workflow manager may include the DoseEdge™ pharmacy workflow manager offered by Baxter Healthcare Corporation of Deerfield, IL In this regard, the healthcare facility 110 may employ a tool that may capture dose order information to generate and/or supplement dose order records corresponding to a dose to be prepared for administration to the patient. This may include capturing dose order data received from an order entry system and/or supplementing the dose order record with dose order metadata regarding the dose to be prepared and/or the preparation of the dose. As described in greater detail below, the dose order records may comprise medical information that may be provided to the data storage device 120.

In turn, the data storage device 120 may be operative to store the information regarding the medication preparations such as, for example, dose order records received from the healthcare facility 110. In this regard, the healthcare facility 110 may provide a dose order record that corresponds to a dose order received from a healthcare provider. One example may be a dose order record generated in response to a provider generating a dose order that is received at a pharmacy for a medication dose to be administered to a patient. Upon receipt of the dose order, the healthcare facility 110 may generate a dose order record corresponding to the dose order.

The dose order record may contain one or more dose order record data fields. The dose order record data fields may be populated with dose order metadata related to the dose order. The dose order metadata may be obtained from a received dose order (e.g., by way of a dose order entry system or the like) or may be associated with the dose order after receipt of the dose order (e.g., by a pharmacy workflow manager or the like during the management, preparation, and/or distribution of the dose corresponding to the dose order). The dose order record data fields may include one or more fields that provide patient identifying information. For instance, the dose order record data fields may include data related to a patient name, geographic data, pertinent dates (e.g., date of birth, date of admission, date of administration, etc.), telephone numbers, fax numbers, email addresses, social security numbers, medical record numbers, health plan beneficiary numbers, account numbers, certificate/license numbers, vehicle identifiers and serial numbers including license plate numbers, device identifiers and serial numbers, uniform resource locators (URLs), Internet protocol addresses, biometric identifiers (i.e. retinal scan, fingerprints), identifying images, or any unique identifying number, characteristic or code. The patient identifier may, in this regard, comprise PHI that is associated with a dose order record.

Other potential dose order record data fields may also be provided that relate to the generation, preparation, distribution, and/or administration of the dose. For instance, such dose order record data fields may include, for instance, a scheduled drug administration date/time, an actual drug administration date/time, a scheduled distribution date/time, an actual distribution date/time, an expiration date for the medication preparation, a dilution value, a count of the number of medical products in the dose, a date/time of entry of the dose order, a volume measure of the dose, a date/time of the first dose of a series of doses, an indicator as to whether the dose is a first dose in a series of doses, an indicator of whether the dose comprises hazardous materials, an indicator of whether the dose is a high risk dose, a dose identifier, an indication of whether the dose is a test dose, a label format for a label corresponding to the dose, a nursing unit corresponding to the dose, order instructions, whether the dose order is on hold, a date/time for when the dose order is to be on hold, an overfill amount for the dose, a basal energy expenditure value for a patient, a body surface area value for a patient, a patient height, a patient weight, a duration for how long a dose is pending, a date/time the dose was prepared, whether a label for the dose order has been printed, at what time the dose order label was printed, the name of the printer to which the dose order label was printed, a rate of administration of the dose, an indication of whether the dose was ever rejected by a pharmacist during preparation, a date/time the dose was rejected, the identity of the pharmacist that rejected the dose, an administration route for the dose, a history of scan events for the dose, a date/time of scan events for the dose, a date/time the dose was sorted, an indication of the dose status, an indication of whether the dose was a stock dose, whether the dose was for total parenteral nutrition (TPN), an indication of the type of TPN associated with the dose, a date/time the dose was verified by a pharmacist, an identify of who verified the dose, an indication of who performed a given step related to the dose, dose preparation documentation (e.g., including images of the dose preparation and/or product preparation for components of the dose order), an error log for the dose or other appropriate information related to the dose. In an embodiment, the dose order record including any one or more of the fields described above may be provided to the data storage device 120.

The data storage device 120 may be located remotely from each healthcare facility 110 with which the data storage device 120 is in communication. In an embodiment, the information received at the data storage device 120 may be a complete data record received from a healthcare facility 110. A complete data record may refer to a data record that contains the same information when received at the data storage device 120 as was contained by the data record at the healthcare facility 110. That is, a complete data record may have no data redacted therefrom. The information received at the data storage device 120 may be dose order records with information related to one or more dose order record fields as described above. Accordingly, the data storage device 120 may thus store a backup copy of the records provided from each respective healthcare facility 110. That is, complete copies of dose order records from the healthcare facility 110 may be provided to and stored on the data storage device 120. Accordingly, the data storage device 120 may include a backup portion 130 that stores the complete data records (e.g., dose order records) received from each respective one of the healthcare facilities 110. As may be appreciated, data provided by the healthcare facilities 110 may be in a proprietary data format that may or may not be readable by third parties without use of corresponding proprietary software executed by the healthcare facility 110.

In an embodiment, the backup data portion 130 may be operative to provide a backup version of data to any one or more of the healthcare facilities 110. For instance, in the event of a data loss at any one or more of the healthcare facilities 110a-110c, the backup data portion 130 may be able to provide a backup copy of a database to the healthcare facility 110 for the purposes of restoring the database. That is, data provided from any respecting one of the healthcare facilities 110 may be provided back to the given healthcare facility 110 as a data backup. As such, provision of the medical information by the healthcare facilities 110 may provide the facilities 110 benefit in the form of a data backup. Thus, medical information that relates to patient health may be efficiently backed up at the backup data portion 130 and available for restoration at the healthcare facility 110 in the event of a data loss at the facility 110.

The data storage device 120 may also include a shareable data portion 150. The shareable data portion 150 may store data records that have at least a portion of the medical information redacted therefrom. For example, in an embodiment, records in the shareable data portion 150 may have personal health information (PHI) removed therefrom. In this regard, a data screening module 140 may be provided. The data screening module 140 may access the complete data records stored in the backup data portion 130. The data screening module 140 may remove one or more portions of data (e.g., PHI or other patient identifying information) from the records. In turn, the redacted data records may be stored in the shareable data portion 150.

As such, the backup data portion 130 and the shareable data portion 150 may be separated such that access to each respective data portion may be controlled. While the data portions may reside on the same device (e.g., a common drive, server, or the like), the data portions may be segregated such that access on one portion may not allow for access to the other. In an embodiment, the data portions may be stored on different corresponding devices.

It may be advantageous to provide associations between the data records correspond to a given patient even if the given patient is not identified (i.e., even if the records are redacted). Thus, the system 100 may be operative to associate redacted records and a patient to determine what medication preparations were associated with a given patient without providing information that identifies the actual patient. As the identity of the patient may comprise PHI, the identity of the patient may be redacted from the record while still providing an associative relationship between all records for a given patient. That is, the data screening module 140 may generate a unique identifier that corresponds to a given patient but is not capable of identifying the patient. As such, all data records associated with that patient may be assigned the unique identifier corresponding to the patient. All data records for the given patient may therefore be identified while the identity of the patient themselves may not be provided.

One example of a unique identifier may comprise a hash value generated by application of a cryptographic hash function to one or more portions of the complete data record prior to storing the redacted record in the shareable portion 150. In turn, the redacted data records may be stored with a generated hash value, which may comprise a unique identifier. In an embodiment, the complete dose record may include one or more patient identifier. For instance, the dose records may include field containing the patient name and/or other identifying information related to the patient such as, for example, a facility identifier for the patient, a date of birth, a social security number, or other patient identifying information as described above. Accordingly, the patient identifier may include PHI. In turn, any one or more of the patient identifiers of the complete dose record may comprise an input to the hash function. The resulting hash value output may provide the unique identifier that may be stored in corresponding relation to the redacted data records stored in the shareable data portion 150.

The data screening module 140 may apply a hash function to one or more patient identifier fields of the complete dose order records. For instance, one or more cryptographic hash functions may be applied such as, for example, SHA-1, SHA-2, SHA-3, MDS, RIPEMD-128/256, RIPEMD-320, RTR0, or other appropriate hash functions now existing or later developed. Preferably, the applied hash function is deterministic. That is, for each given unique input a corresponding unique output is provided by the function without data collisions. Furthermore, the hash function is preferably non-invertable. For example, when provided with a hash value resulting from the hash function, the input that resulted in the hash value should not be ascertainable. Thus, the hash function preferably provides a one-way conversion of the patient identifier to a non-identifying unique value that is unique for each given one of a plurality of patients. In turn, the unique value for a given patient may be the same each time the hash function is applied. Thus, two or more different dose order records associated with a given patient may both receive the same unique identifier upon application of the hash function to the records. As such, a review of the resulting redacted dose order records containing the unique identifier in place of a patient identifier may allow for dose order records corresponding to a given patient may be identified based on a common unique value (e.g., a hash value). The hash value may also be further encoded, e.g. using Base64 encoding on the resulting hash value.

The system 100 may also include a collaboration module 160. The collaboration module 160 may access the shareable data portion 150 containing the redacted data records. In turn, the collaboration module 160 may retrieve the redacted data records for transformation into a format that may be useable by one or more remote users 170 and/or local users 165 of the system 100. The format into which the collaboration module 160 transforms the redacted data may be at least partially based on a predetermined operational need of the local user 165 or remote user 170 that requests the data from the collaboration module 160.

The collaboration module 160 may facilitate selective, secure access to local users 165 and/or remote users 170 who wish to access the formatted data extracted by the collaboration module 160 from the shareable data portion 150. In this regard, a plurality of access layers may be provided that must be satisfied by users prior to accessing the formatted data from the shareable data portion 150. For instance, the remote user 170 may be required to access a first layer such as a virtualized private network (VPN) or the like. Accessing the VPN may require a remote user 170 to provide appropriate credentials (e.g., a valid user name and password combination, a cryptographic key, a one-time password, a biometric value, etc.). A local user 165 may be required to be utilizing an access terminal on a common network with the collaboration module 160 (e.g., a local area network or the like). A user may then access the collaboration module 160 with further credentials (e.g., a valid user name and password, a cryptographic key, a one-time password, a biometric value, etc.). Once the user has joined the VPN or accessed the collaboration module 160 on a common network and provided the necessary credentials to access the collaboration module 160, the user may have access to the formatted data at the collaboration module 160 based on the redacted data records in the shareable data portion 150. As such, a plurality of access layers may be provided to reduce unauthorized access to the shareable data portion 150.

The collaboration module 160 may access the redacted data records in the shareable data portion 150 and extract the data therefrom. In turn, the collaboration module 160 may transform the data into a given format that is loaded (e.g., to a storage device at the collaboration module 160 and/or in the shareable data portion 150) for access by users 165/170. The format of the data may comprise a standardized format. The standardized format may in turn be accessible by all those who access the collaboration module 160. The standardized format may include an extensible markup language (XML) format. The standardized format may additionally or alternatively be provided as a delineated text file, a pivot table, or any other standardized format or data view. In this regard, data that may be provided in a proprietary format (e.g., as described above) may in turn be formatted such that the data may be accessed and/or viewed by other parties/ users that are incapable of viewing the data in the proprietary format provided. As such, the data may be more widely disseminated to provide further data analytics relative thereto.

In an embodiment, the collaboration module 160 may format the redacted data from the shareable data portion 150 into a format at least in part based on the user who is to access the data, an application in which the data is to be used, a requested format of the user, and/or other appropriate criteria. For instance, different remote users 170 may have access to the collaboration module. As described above, access to the collaboration module 160 by a remote user 170 may include one or more layers of access protocols that require authentication including, for example, providing a user name and password. In this regard, access to the collaboration module 160 may at least in part identify the remote user 170 accessing the collaboration module 160. In this regard, the format of the data to which a remote user 170 has access may at least depend on the identity of the user 170. For instance, a first remote user 170 may be associated with a first party and receive the formatted data in a first format associated with the first party (e.g., a proprietary data format corresponding to the first party). A second remote user may be associated with a second party and receive the formatted data in a second format associated with the second party (e.g. a proprietary format associated with the second party). The first and second formats may be different and may be unique to the particular user accessing the collaboration module 160. As will be described in greater detail below, different remote users 170 of the formatted data provided by the collaboration module 160 may have different operational needs as it relates to the data stored in the shareable data portion 150. As such, the format of the data presented to a user 165/170 may be based on an anticipated use of the data and/or a requested format by the user 165/170.

As may be appreciated in FIG. 1, the data storage module 120 and collaboration module 160 may collectively comprise a collaboration system 305. In this regard, the healthcare facilities 110a-110c may comprise data sources that provide data to the collaboration system 305. In turn, users 170 and/or 165 may access the data provided by the data sources 110a-110c by utilizing the collaboration system 305. In this regard, the embodiment depicted in FIG. 1 provides one exemplary embodiment of a collaboration system 305, however as will be appreciated in further reference to FIG. 2 below, other embodiments of collaboration systems 305 are contemplated.

Furthermore, the various components depicted in FIG. 1 may be in operative communication over one or more networks. That is, the various modules and devices depicted may each be in operative, networked communication. The network communications may utilize a wide area network such as the Internet or the like. Additionally or alternatively, the communications may be by way of one or more local area networks, intranets, private networks, or the like. Furthermore, the modules and devices may comprise integrated systems or may be provided discretely. For instance, in an embodiment, the data storage device 120 may include discrete hardware for each of the backup data portion 130 and the shareable data portion 150. For instance, each respective data portion may be provided on separate hardware such as separate hard drives, separate servers, or the like. Alternatively the portions may comprise segregated data spaces on a common device such as a common hard drive, a common server, or the like. In this same regard, the data screening module 140 and/or collaboration module 160 may each be stand alone modules executing on discrete hardware devices or either module may be executed on a common hardware device that may or may not also contain the backup data portion 130 and/or the shareable data portion 150.

Figure 2:
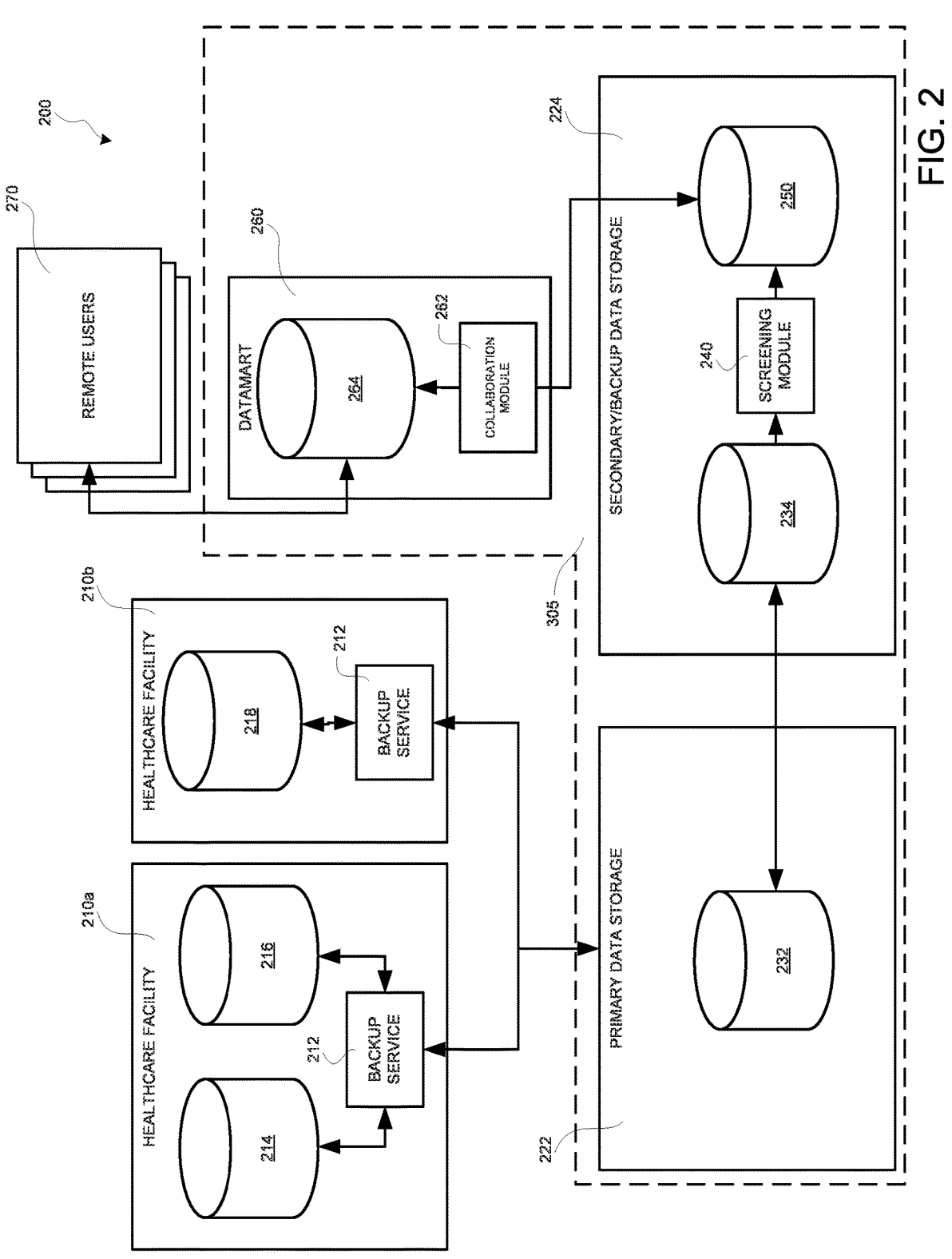
FIG. 2 is a schematic view of an embodiment of a system for exchange of information related to medication preparations.

FIG. 2 depicts another embodiment of a system 200 for exchange of information. The variations and details described above in relation to FIG. 1 may be applicable to the system 200 of FIG. 2 unless specified otherwise. The system 200 generally includes healthcare facilities 210a and 210b that are in operative communication with a primary data storage device 222. The primary storage device 222 may be in operative communication with a secondary or backup data storage device 224. In turn, a datamart module 260 may be in operative communication with the backup data storage device 224. Remote users 270 may access the datamart module 260. In turn, medical information received from the healthcare facilities 210a and 210b may be selectively provided to the remote users 270 for advantageous data analytics relative thereto.

As shown in FIG. 2, each healthcare facility 210 may include a backup services module 212. The backup services module 212 may be in operative communication with one or more local database of the healthcare facility. For instance, the backup service module 212 at the healthcare facility 210a may be in operative communication with local databases 214 and 216. In this regard, local databases 214 and 216 may store information at the healthcare facility 210a. Backup service 212 at healthcare facility 210b may be in operative communication with a local database 218 at healthcare facility 210b. In an embodiment and as described above, the information may include dose order records corresponding to dose orders for medication preparations to be administered to a patient.

In any regard, the backup service module 212 may access a local database at the healthcare provider 210 and provide information to the primary data storage device 222. The backup service module 212 may periodically poll the one or more databases with which it is in operative communication and provide any new or modified records to the primary data storage device 222. Alternatively, the backup service module 212 may continuously monitor one or more database and provide records to the primary data storage 232 in a real time or near real time basis.

The backup service module 212 may also apply a local backup policy established by each respective healthcare facility 210. For instance, a healthcare facility 210 may wish not to provide information containing certain data fields (e.g., those fields corresponding to patient identifiers and/or PHI) to the primary data storage device 232. In this case, the backup service 212 may facilitate redaction of one or more portions of the data from the data prior to providing the data to the primary data storage device 232. In an embodiment, the backup service module 212 may be operative to generate a unique identifier corresponding with a given patient as was discussed above in connection with the data screening module 140. That is, the backup service module 212 may locally generate a unique value that uniquely associates a given patient with one or more data records, yet is non-identifying of the patient. As such, the backup service 212 may be operative to apply a hash function to the data records to redact a patient identifier from the records. In turn, the information provided from the backup service 212 to the primary data storage device 222 may include a unique identifier in lieu of patient identifying information.

The primary data storage device 222 may include a backup data portion 232 at the primary data storage device 222. The primary data storage device 222 may also be in operative communication with a backup data storage device 224. The backup data storage device 224 may include a backup data portion 234. The backup data portion 232 of the primary data storage device 222 may be replicated and stored in the backup data portion 234 of the backup data storage device 224. The primary data storage device 222 and the backup data storage device 224 may be distributed at distinct geographic locations. For example, the primary data storage device 222 may be located at a first geographic location on the east coast of the United States and the backup data portion 224 may be located at a second geographic location on the west coast of the United States. Periodically, the primary data storage device 222 may communicate data from the backup data portion 232 to the backup data portion 234 of the backup data storage device 224. As such, a backup of the backup data portion 234 may be stored at each location. Accordingly, the use of geographically distributed storage device locations may reduce the potential for data loss at both facilities simultaneously. Thus, in addition to the primary data storage device 222 facilitating data backup services for the healthcare facilities 210, a further backup potential is created by use of the backup data storage device 224. As such, in the event of a data loss at a healthcare facility 210 and/or the primary data storage device 222, the backup data storage device 224 may provide backup copies of data to the facility 210 and/or primary data storage device 222 to facilitate data recovery.

The backup data storage device 224 may include a data screening module 240. Although, the data screening module 240 could be located at the primary data storage device 224 in addition to or as an alternative to the backup data storage device 224 without limitation. In either regard, the operation of the data screening module 240 would be the same. As described in relation to FIG. 1, the data screening module 240 may generate a unique identifier associated with a patient identifier for the purpose of redacting a portion of the data records (e.g. including patient identifiers and/or PHI) to be stored in a shareable data portion 250 at the backup data storage device 224. In the embodiment depicted in FIG. 2, data records may be provided in a redacted form from the backup service module 212 at the healthcare facility. In this regard, the data screening module 240 may further redact the data records or pass the previously redacted records on to the shareable data portion 250. In any regard, the information stored in the shareable data portion 250 may be redacted (e.g., the data may have patient identifiers and/or PHI removed therefrom).

The shareable data portion 250 may be in operative communication with a collaboration module 262. The collaboration module 262 may be provided in a datamart module 260. The datamart module may allow for the collaboration module 262 to extract, transform (e.g., format), and load formatted data into a datamart storage device 264 for access by remote users 270. Again, the formatted data may be provided in a standardized form or may be provided in particular given forms accessible by the remote users 270 as discussed above.

In this regard, FIG. 2 depicts another embodiment of a collaboration system 305 the comprises the primary data storage device 222, the backup data storage device 224 and the data more module 260. In this regard, collaboration system 305 may include geographically remote backup data storage devices for the purpose of providing additional data redundancy. In this regard, the healthcare facilities 210*a* and

210*b* may comprise data sources that provide medical information to the collaboration system 305. In turn, the collaboration system 305 may provide access to the redacted and formatted medical information to remote users 270.

Figure 3:
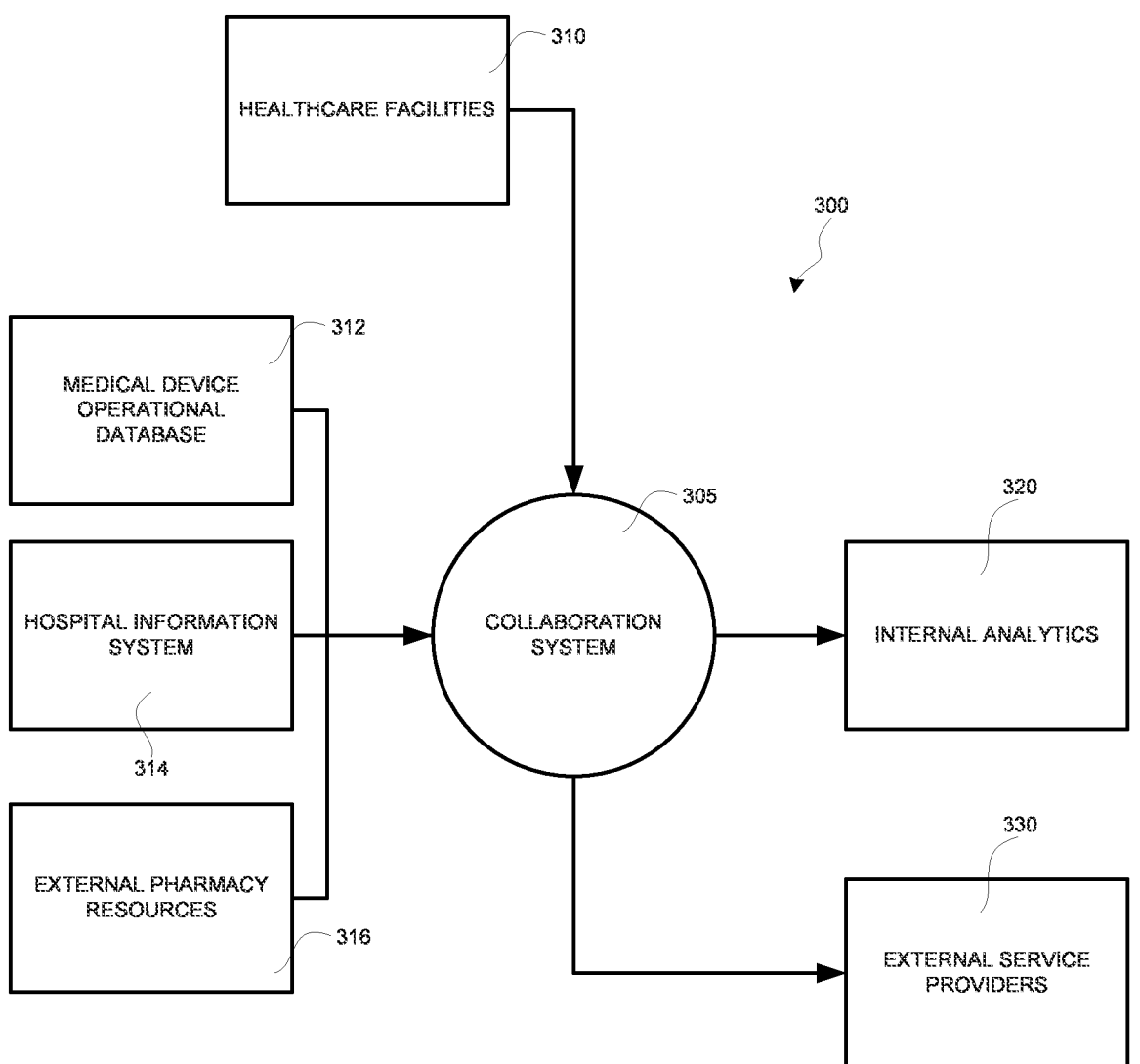
FIG. 3 is a schematic view of an embodiment of a collaboration platform with collaborative data analytics relative to shared information related to medication preparations.

FIG. 3 depicts a schematic view of an embodiment of a collaboration platform 300 that may be used to provide medical information from one or more data sources to users for the purpose of facilitating data analytics on the medical information. The collaboration platform 300 may include a collaboration system 305. The collaboration system 305 may comprise a system such as collaboration system 305 described above in relation to system 100 shown in FIG. 1 or collaboration system 305 shown in FIG. 2. In any regard, the collaboration system 305 may receive information from a healthcare facility 310. In turn, the information may be provided in a shareable data portion of the collaboration system 305 for access by users such that the information received from the healthcare facilities 310 is transformed prior to access by one or more third parties. For instance, the transformation may include redacting patient identifiers and/or PHI from the data and/or transforming the data into a format useful to users of the system 305.

However, the collaboration system 305 may also be in operative communication with one or more other sources of data in addition or as an alternative to the healthcare facilities 310. For instance, the collaboration system 300 may be in operative communication with a medical device operational database (e.g., a dose administration device database or other appropriate source of medical device information), a hospital information system 314, external pharmacy resources 316, and/or any other appropriate source of medical information. In the event the medical information received from the data source (e.g., the healthcare facility 310, the medical device operational database, the hospital information system 314, the external pharmacy resources 316 and/or any other appropriate source of medical information) contains information to be redacted (e.g., patient identifiers and/or PHI), the collaboration system 305 may be operative to redact the medication information and, for instance, generate a unique identifier that is related to, but does not identify a patient as described above.

The collaboration system 305 may provide access to formatted data generated from one or more data sources. The data provided by the collaboration system 305 may include redacted data records with patient identifiers and/or PHI removed therefrom regardless of the source of the data. The data provided by the collaboration system 305 may also be formatted as described above in relation to the embodiments of collaboration modules discussed above. The collaboration system 305 may thus format data from a plurality of sources that may originate in different formats. As such, the collaboration system 305 may be operative to combine and/or aggregate data from the different sources for presentation to users in a standard or particular format.

The collaboration system 305 may, thus, aggregate and format a large amount of medical data from a plurality of sources. In turn, users may access the aggregated and formatted data of the collaboration system 305. Such users may be local users 320 that locally access the collaboration system 305 (e.g., are users on a common network with the collaboration system 305 such as users of a local area network, intranet, or the like). Thus, internal analytics within a given organization may be facilitated. Furthermore, external users 330 may access the collaboration system 305 (e.g., users that access the system 305 by way of a wide area network or the like). In turn, internal analytic users 320 and/or external service providers 330 may have access to the collaboration system 305. The format available to and/or accessible by different users may depend upon the user's identity, whether the user is an internal or external user, and/or a given purpose for which the user is accessing the data.

The modules described herein may comprise software, hardware, or a combination of both. For instance, the modules of the system may include specifically configured hardware such as application specific integrated circuits (ASICs), programmable field gate arrays, or other appropriate processors. In an embodiment, the modules may include a microprocessor in operative communication with a memory. The memory may comprise a non-transitory computer readable medium that may include machine-readable instructions. As such, the processor may access the memory and be specifically configured by the machine-readable instructions stored therein to execute any of the functionality described herein. Additionally, the modules described above may be executed using a common processor in operative communication with a memory that provides the functionality of a plurality of modules. In this regard, the modules may be executed using a single common processor or different modules may be executed using different processors.

Turning to FIG. 4, an embodiment of a method 400 for exchange of medical information by way of a collaboration platform is depicted in the form of flow chart. The method may include collecting 402 information from one or more data sources. As described above, the data sources from which medical information is collected may include healthcare facilities, medical device operational databases, hospital information systems, external pharmacy resources, or any other appropriate sources of medical information. In turn, the method 400 may include storing 404 medical information in a backup data portion. As described above, the shareable data portion may comprise a portion of a data storage device.

In an embodiment, the method 400 may include creating 406 backup data records. The back of data records may comprise a copy of complete records stored in the backup data portion. The backup data records may be stored in a remote geographic location separate from the backup data portion stored in step 404. In turn, the backup data records may be used to restore lost or corrupted data at a healthcare facility and/or other data source.

The method 400 may also include accessing 408 the complete medical information (e.g., the complete data records). As described above, it may be beneficial to redact a portion of the complete data records to, for example, remove patient identifying information therefrom. In this regard, the method 400 may include redacting 410 one or more portions of information from the medical records accessed at step 408. As described above, the redacting 410 may include applying a hash function to generate hash value based at least in part on a portion of the data records including, for example, a patient identifier and/or PHI. The method 400, in turn, includes storing 412 the redacted medical information in a shareable data portion. The shareable data portion may be separate from the backup data portion such that selective access to either portion may be separately facilitated.

In an embodiment, the method 400 includes extracting 414 the redacted records from the shareable data portion. The method 400 may further include formatting 416 redact data records into a data format that may be useful to a user accessing the redacted records (e.g., for purposes of data analytics). In this regard, the format may be standardized format presented all users of the system or may be particularly directed to a particular user and/or data analytic context for which the data is to be used. The method 400 may further include loading 418 the formatted redacted records (e.g., by a collaboration module or the like) to facilitate access to the formatted redacted records. In turn, the method 400 may include permitting 420 selective, secure access to the formatted redacted data records by users of the platform. As described above, the users may each have access to a standardized format or may be presented with a specific format of data based on the identity user, and indicated application for which the data is to be used, or a requested format type by the user.

In turn, the medical information collected 402 from the various sources of medical information may be transformed and made available to users to perform, for example, data analytics on the medical information. Accordingly, the method 400 may include performing 422 data analytics with respect to the formatted redacted records there selectively accessed 420. Examples data analytics may include, for example, monitoring trends with respect to ordered doses for the purpose of improving patient safety relative to the ordered doses and/or improving business opportunities by gaining actionable business intelligence data relative to the activities corresponding to the medical information gained from the one or more sources. Other data analytics may be contemplated such as those described in greater detail below. In this regard, the data analytics may be provided in the form of the plurality of services by users may access and/or perform data analytics on the redacted, formatted medical information in a cloud architecture (e.g., using networked resources) to facilitate improved efficiency, speed, and/or utilization of resources relative thereto.

Figure 5:
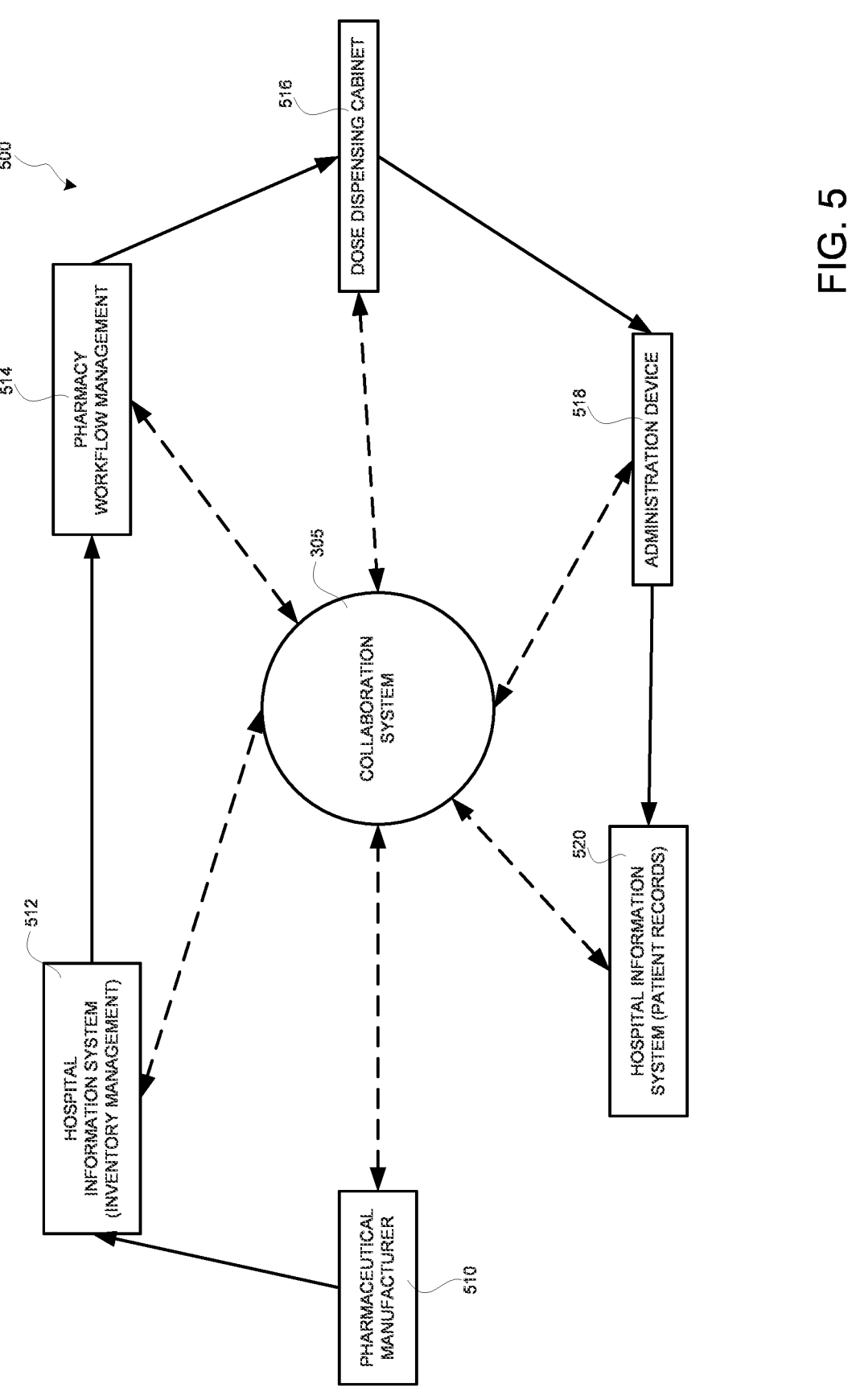
FIG. 5 is a schematic view of an embodiment of an implementation of a collaboration platform for exchange of medical information in a particular context including dose preparation and administration.

FIG. 5 depicts an embodiment of a platform 500 utilizes a collaboration system 305 aggregate data in turn provide redacted formatted data to one or more users who in turn access the data. As such, the collaboration system 305 may comprise a collaboration system according to the embodiment of a collaboration system 305 depicted in FIG. 1 and/or embodiment of a collaboration system 305 depicted in FIG. 2. Furthermore, any other appropriate combination of modules, components, or other devices comprising a collaboration system 305 and provided that facilitates redaction and formatting of medical information provided from one or more sources. In this regard, collaboration system 305 may include additional or fewer modules than those described with respect to the specific embodiments described in FIGS. 1 and 2. As such, the embodiments depicted in FIG. 1 and FIG. 2 are exemplary, but not limiting.

In FIG. 5, the collaboration system 305 is discussed in relation to the context of preparation of a dose for a patient. In this regard, the solid arrow lines in FIG. 5 may represent flow of physical goods between the various entities described. The dash-dot lines in FIG. 5 represent flow data between the various entities in the collaboration system 305. Accordingly, the platform 500 shown in FIG. 5 represents one particular application of a collaboration system 305 is a relates to the flow of materials in connection with preparation and administration of the dose to the patient and healthcare facility.

The platform 500 may include a pharmaceutical manufacturer 510. The pharmaceutical manufacturer 510 may manufacture a medical product of a dose such as a drug compound and/or other intermediaries including diluents or the like. Accordingly, the pharmaceutical manufacturer 510 may provide the manufactured medical product to a hospital that employs a hospital information system 512. Specifically, an inventory management system at a healthcare facility may be executed by the hospital information system 512 may allow for receipt and tracking of goods from the pharmaceutical manufacturer 510.

The pharmaceutical manufacturer 510 may also provide data to the collaboration system 305. In this regard, the pharmaceutical manufacturer 510 may comprise a data source that provides medical information collaboration system 305. Examples of pertinent data that the pharmaceutical manufacturer 510 may provided the collaboration system 305 may include for example, medical product identifiers, lot numbers, expiration dates, inventory management numbers, product concentrations, product sizes, or other information related to medical products manufactured by the pharmaceutical manufacturer 510.

The inventory management component of the hospital information system 512 may, after receipt of medical products from the pharmaceutical manufacturer 510, monitor the medical products including, for example at time in which a medical product is requested at a pharmacy and/or track information associated with medical products including, for example lot numbers, expiration dates, product identifiers, or the like. As such, a pharmacy workflow manager 514 may be provided in the pharmacy of a healthcare facility. The pharmacy workflow manager 514 may receive products from the inventory management system of the hospital information system 512. For instance, the pharmacy workflow manager 514 may request medical products for use in preparation of doses from the inventory management system 512. As such, inventory management system 512 may facilitate provision of medical products to the pharmacy for tracking by the pharmacy workflow manager 514.

The inventory management portion of the hospital information system 512 may also provide data to the collaboration system 305. Exemplary data may include, for example, average inventory levels, current inventory levels, inventory supply parameters including average durations a medical product is maintained in stock prior utilization, and/or data concerning the movement of medical products within a hospital including, for example, provision of drug products to the pharmacy workflow manager 514 for use in preparation of a dose.

The pharmacy workflow manager 514 may facilitate preparation of doses for administration to patients. As described above, the preparation of doses may be in response to received dose orders from healthcare providers or the like. As such, the pharmacy workflow manager 514 may receive dose order information as described above. Furthermore, the pharmacy workflow manager 514 may supplement such data with information related to the preparation of the dose. For example, images may be captured related to the medical product(s) utilized to prepare the dose. Furthermore, data may be gathered from medical products and used to populate specific dose order records corresponding to a dose order. The dose order may or may not be patient specific. In this regard, the dose order record may include information regarding a lot number or an expiration date of a medical product used to prepare the dose. Additionally, the pharmacy workflow manager 514 may supplement data such as the identity of the pharmacy technician who prepared the dose, the pharmacist who approved the dose, as well as parameters related thereto such as the time/date when such events occurred. Furthermore, the pharmacy workflow manager 514 may present to a pharmacy technician a protocol for use in preparation of the dose. The specific protocol utilized may also be associated with the dose order record.

The pharmacy workflow manager 514 may also provide data to the collaboration system 305. In this regard, the one or more portions of the data described above that is the generated and/or received by the pharmacy workflow manager 514 may be provided. In this regard, the pharmacy workflow manager 514 may provide information related to the preparation of a dose and/or related to the medical product(s) used to prepare the dose. Furthermore, the data provided by the pharmacy workflow manager 514 to the collaboration system 305 may include information related to the time/date at which certain events relative to the dose order occur. The pharmacy workflow manager 514 may also detect errors that occur during the preparation of the dose order. For example, a pharmacy technician may scan an incorrect medical product to be used in connection with the dose to be prepared. While the pharmacy workflow manager 514 may alert the pharmacy technician of the error such that it may rectified, the pharmacy workflow manager 514 may further record the performance of the error in connection with the dose order with which it occurred.

The pharmacy workflow manager 514, upon dispensation of a dose from the pharmacy, may provide the dose to a dose dispensing cabinet 516. The dose dispensing cabinet 516 may be accessible by patients, healthcare facility personnel, or others to retrieve a dose once prepared. This regard, the dose dispensing cabinet 516 may track and/or collect certain information related to the dose. Examples of such data may include the time a dose is placed or retrieved in the dispensing cabinet 516 prior to retrieval, the identity of a person stocking and/or retrieving a dose from the dose dispensing cabinet 516, number of available doses in the dispensing cabinet 516, the number of free storage areas in the dose dispensing cabinet 516, or other relevant data. The dose dispensing 516 may also track errors related to the retrieval of dose orders from the dose dispensing 516. For example, unauthorized attempts to access storage location may be recorded. Furthermore, erroneous attempts to access storage location or attempt to access the incorrect story location may also be tracked. As such, any or all the data collected or available to the dose dispensing cabinet 516 may also be provided to the collaboration system 305.

Once the dose is retrieved from the dose dispensing cabinet 516, the dose may be administered to a patient using an administration device 518. That is, healthcare facility personnel such as a nurse or the like may retrieve a dose from the dose dispensing cabinet 516. The dose may in turn be connected to an administration device 518. The administration device 518 may, for example, be an infusion pump utilized to deliver the dose to a patient. In this regard, the administration device 518 may record information regarding the dose administered such as, the patient to which the doses administered, or other relevant information such as the time of administration, parameters regarding the administration (e.g., administration rate, administration duration, etc.), or other information collected regarding the administration of the dose. The administration device 518 may further provide any such information it has access to or generates to the collaboration system 305.

Once doses are delivered to a patient, a patient record portion of a hospital information system 520 may be updated to record the administration of the dose to the patient. For example, parameters such as the hospital personnel responsible for the administration of the dose, the time/date of the dose, or other relevant medical record information including health care provider notes or the like be recorded in the patient records of the hospital information system 520. Furthermore, this information may also be provided to the collaboration system 305. The administration device 518 may further track errors. For example, the administration device 518 may include checks to ensure proper programming of the administration device 518. In the event that an improper programming is made, the error may be recorded by administration device 518.

Accordingly, the collaboration system 305 may collect information from the various stages related to the manufacture, preparation, and/or administration of the dose to the patient. As described above, the collaboration system 305 may aggregate, redact, and format such data. In turn, the collaboration module of the collaboration system 305 may allow access to the aggregated, redacted, and formatted data for purposes of data analytics. As briefly stated above, it may be valuable for the sources of data (e.g. any one or more of the entities described in FIG. 5) to not only provide data to collaboration system 305, but also retrieve data from the collaboration system 305 for a number of different reasons. As may be appreciated in FIG. 5, the entities shown may not only provided to collaboration system 305 may also each comprise users that in turn have access to the collaboration system 305 to access the aggregated, redacted, and formatted data. In this regard, by virtue the collaboration system 305 providing redaction and formatting, any one or more of the entities shown in FIG. 5 may have access to a shareable data portion of the collaboration system 305 to gain access to data for use in data analytics.

This may open the available data to each one of the specific entities beyond that for which they are solely responsible. That is, the pharmaceutical manufacturer 510 may access the collaboration system 305 to obtain data related to the hospital information system 512 and/or 520, a pharmacy workflow manager 514, a dose dispensing cabinet 516, or an administration device 518. Absent the collaboration system 305, the collection in or use of such data may be arduous at each individual one of the entity shown in FIG. 5 may be required to solicit information directly from other entities and be subjected to concern such as data privacy and security. However, the collaboration system 305 may provide a central aggregation, redaction, and formatting of a pool of shared data that in turn provides efficient access to data for purposes the data analytics beyond that available for each individual entities on portion of the data supplied to collaboration system 305.

Some relevant examples of data analytics that made performed utilizing the platform 500 shown in FIG. 5 may include analysis that provides for improved patient safety, medical results, inventory management, business insight, security, or other useful outcomes related to the data analysis. For example and as described above, errors may be tracked at one or more the pharmacy workflow manager 514, dose dispensing cabinet 516, or administration device 518. In an effort to improve patient safety, a pharmaceutical manufacturer 510 may review data provided by the collaboration system 305. As the data aggregated by the collaboration system 305 may provide insights to the occurrence of errors with respect to a number of parameters including a particular medical product utilized to prepare the dose, the pharmaceutical manufacturer 510 may determine if error rates at any one or more of the pharmacy workflow manager 514, dose dispensing 516, or administration device 518 are more prevalent with a particular medical product. Identification of such trends may in turn allow the pharmaceutical manufacturer 510 to determine a root cause of a source of the error and remedy the root cause. For example, in the pharmacy workflow manager 514, confusing labeling of packaging may result in an increased error rate with respect to a particular medical product. In turn, the pharmaceutical manufacturer 510 may identify the increased error rate with respect to the medical product and in turn launch a root cause analysis. In turn, a source of the error in the form of the confusing labeling may allow the pharmaceutical manufacturer 510 to improve the labeling and reduce the errors associated with the medical product.

Similarly, one or more of the entities in FIG. 5 may be interested in analytics with respect to inventory for purposes of improving supply-chain characteristics at any one or more portions of the supply chain between the pharmaceutical manufacturer and the administration of the dose to the patient. For example, the data provided by the collaboration system 305 allow for analytics with respect to turnaround times, throughput of doses, cycle times, or the like. Furthermore, information provided the various sources of data may allow for analysis with respect to the best source doses. For example, a pharmacy workflow manager 514 may determine, based on data analyzed from the collaboration system 305, whether it is more efficient to produce a dose within the pharmacy or, for example, buy premade doses from an outside vendor. Furthermore, an entity responsible for a dose dispensing cabinet 516 may utilize data retrieved the collaboration system 305 determine whether diversion a product from the dose dispensing cabinet is occurring.

In this regard, number of valuable parameters contained within the data provided by the collaboration system 305 may be leveraged to provide useful insights during data analytics. Specifically, given the foregoing discussion regarding the de-identifying of medical information while preserving the ability to associate various portions of the medical information with a given patient, patient specific analysis may be undertaken. This may be useful for providing insight regarding administration of doses to particular patient. For example, the delay between dose order entry and dose administration may be examined with respect particular patients. In turn, correlations with respect to types of medication, administration routes of medication, the nursing unit associated with the doses, or even facilities in general, can be made. That is, metrics with regard to these various parameters may be examined in connection with delays between dose order and administration to provide increases in efficiency for the process of preparing and administering the doses to a patient. Such may be particularly valuable in urgent or "STAT" doses with the understanding that the time sensitivities associated with such doses may be critical to patient outcomes in certain instances such as an emergency context.

While the invention has been illustrated and described in detail in the drawings and foregoing description, such illustration and description is to be considered as exemplary and not restrictive in character. For example, certain embodiments described hereinabove may be combinable with other described embodiments and/or arranged in other ways (e.g., process elements may be performed in other sequences). Accordingly, it should be understood that only the preferred embodiment and variants thereof have been shown and described and that all changes and modifications that come within the spirit of the invention are desired to be protected.

What is claimed is:

1. A system for an exchange of information related to dose preparation, the system comprising:
   a data storage device in operative communication with a plurality of healthcare facilities, wherein the data storage device is configured to receive, from the plurality of healthcare facilities, information regarding a plurality of dose preparations prepared at the plurality of healthcare facilities, wherein the data storage device comprises (i) a shareable data portion that stores redacted data records for each of the plurality of dose preparations having patient identifying information removed therefrom, and (ii) a backup data portion that simultaneously stores data records for each of the plurality of dose preparations including the patient identifying information, and wherein the shareable data portion is configured to have a first network access for remote users and the backup data portion is configured to have a different, second network access such that the backup data portion is not accessible through the first network access and the shareable data portion is not accessible through the second network access; and a processor that is in operative communication with the data storage device, the processor configured to perform a cryptographic operation on the patient identifying information to create a unique hash value when the information regarding the plurality of dose preparations is received from the plurality of healthcare facilities, create redacted data records, each storing the unique hash value instead of the patient identifying information, and store the redacted data records to the shareable data portion.

2. The system of claim 1, wherein the patient identifying information comprises protected health information (PHI) that at least comprises a patient identifier.

3. The system of claim 2, wherein each of the unique hash values includes a unique identifier that associates one or more portions of the information regarding the respective patient without providing identifying characteristics relative to the patient.

4. The system of claim 3, wherein the unique identifier comprises the first unique hash value that is generated in response to the application of the cryptographic operation to the patient identifier.

5. The system of claim 1, wherein the processor is part of the data storage device for generating the redacted data records that are stored in the shareable data portion.

6. The system of claim 1, wherein the processor is located at the plurality of healthcare facilities for generating the redacted data records that are received at the data storage device for storage in the shareable data portion.

7. The system of claim 1, wherein each of the unique hash values comprises a deterministic, non-invertible value based on the patient identifier.

8. The system of claim 1, wherein the backup data portion comprises complete data records including the patient identifying information corresponding to at least a portion of the information regarding the plurality of dose preparations received from the plurality of healthcare facilities.

9. The system of claim 8, wherein the backup data portion and the shareable data portion are separately accessible on the data storage device.

10. The system of claim 1, further comprising a collaboration module configured to provide a plurality of users selective and secure access to the shareable data portion based on a plurality of security layers applied to access the shareable data portion.

11. The system of claim 1, wherein the data storage device comprises a data storage server located remotely from the plurality of healthcare facilities.

12. The system of claim 1, wherein the data storage device comprises a plurality of mirrored data servers distributed at distinct geographic locations.

13. The system of claim 1, wherein the information regarding the plurality of dose preparations comprises dose order records generated in response to received dose orders for the plurality of dose preparations to be administered.

14. The system of claim 1, wherein the information regarding the plurality of dose preparations is received at the data storage device in accordance with a local data policy of each respective one of the plurality of healthcare facilities.

15. A method for generating shareable information regarding dose preparation, the method comprising:

receiving, from a plurality of healthcare facilities, information regarding a plurality of dose preparations prepared at the plurality of healthcare facilities;

storing the information as a backup data portion stored on a data storage device in the form of data records for each of the plurality of dose preparations including patient identifying information;

storing the information as a shareable data portion stored on the data storage device information in the form of redacted data records for each of the plurality of dose preparations having the patient identifying information removed therefrom;

configuring a first network access for remote users and the backup data portion is configured to have a different, second network access such that the backup data portion is not accessible through the first network access and the shareable data portion is not accessible through the second network access;

before storing the information as the shareable data portion, performing, via a processor, a cryptographic operation on the patient identifying information to create a unique hash value when the information regarding the plurality of dose preparations is received from the plurality of healthcare facilities;

storing, via the processor to the data storage device, the unique hash value to each of the redacted data records instead of the patient identifying information; and loading, via the processor, the redacted data records into a remotely accessible storage location for access by users remote from the remotely accessible storage location.

16. The method of claim 15, wherein the patient identifying information comprises protected health information (PHI) that comprises at least a patient identifier.

17. The method of claim 15, wherein the storing further comprises generating the unique identifier in response to applying the cryptographic operation to the patient identifier.

18. The method of claim 15, further comprising providing a plurality of users selective and secure access to the redacted data records.

19. The method of claim 15, further comprising analyzing the redacted data records without the particular identity of the respective patients, wherein the analyzing comprises at least one of error analysis, inventory management, or supply chain management.

20. The method of claim 15, wherein receiving the information regarding the plurality of dose preparations is at least partially based on a local data policy of each respective one of the plurality of healthcare facilities.

\* \* \* \* \*